United States Patent [19]
Garbarino et al.

[11] Patent Number: 5,955,573
[45] Date of Patent: *Sep. 21, 1999

[54] UBIQUITIN-LYTIC PEPTIDE FUSION GENE CONSTRUCTS, PROTEIN PRODUCTS DERIVING THEREFROM, AND METHODS OF MAKING AND USING SAME

[75] Inventors: Joan Garbarino, Berkeley, Calif.; Jesse Jaynes, Raleigh, N.C.; William Belknap, Albany, Calif.

[73] Assignee: Demegen, Inc., Durham, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/505,486

[22] Filed: Jul. 21, 1995

Related U.S. Application Data

[60] Division of application No. 08/279,472, Jul. 22, 1994, abandoned, which is a continuation-in-part of application No. 08/231,730, Apr. 20, 1994, abandoned, which is a continuation-in-part of application No. 08/225,476, Apr. 8, 1994, abandoned, which is a continuation-in-part of application No. 08/148,491, Nov. 8, 1993, abandoned, and application No. 08/148,889, Nov. 8, 1993, abandoned, which is a continuation-in-part of application No. 08/039,620, Jun. 4, 1993, abandoned, said application No. 08/148,491, is a continuation-in-part of application No. 08/039,620.

[51] Int. Cl.[6] ..................................................... A61K 38/00
[52] U.S. Cl. ............................. 530/324; 530/858; 514/12
[58] Field of Search .................................... 530/324, 858; 514/12

[56] References Cited

U.S. PATENT DOCUMENTS

| 5,294,605 | 3/1994 | Houghten et al. | 514/13 |
| 5,357,044 | 10/1994 | Lai et al. | 530/350 |

FOREIGN PATENT DOCUMENTS

| 0342926 | 11/1989 | European Pat. Off. . |
| 0552559 | 7/1993 | European Pat. Off. . |
| 9012866 | 11/1990 | WIPO . |
| 9416076 | 7/1994 | WIPO . |

OTHER PUBLICATIONS

N.E. Hoffman et al., "Isolation and characterization of . . . ubi3", Plant Molecular Biology 17, pp. 1189–1201, 1991.
J.E. Garbarino et al., "Isolation of a ubiquitin–ribosomal . . . plants", Plant Molecular Biology 24, pp. 119–127, 1994.
J.E. Garbarino et al., "Isolation of a Polyubiquitin . . . Plants", Plant Physiol. 109, pp. 1–8, 1995.

*Primary Examiner*—Robert A. Wax
*Assistant Examiner*—Lisa J. Hobbs
*Attorney, Agent, or Firm*—Rothwell, Figg, Ernst & Kurz

[57] ABSTRACT

Stabilized ubiquitin-lytic peptide fusion polypeptides and a method of making the same by sub-cloning nucleic acid sequences coding for lytic peptides into a plasmid vector comprising a promoter and ubiquitin polypeptide coding sequence, wherein the ubiquitin polypeptide sequence is linked to the 5' end of the lytic peptide nucleic acid sequence and is translated as a fusion polypeptide.

6 Claims, 2 Drawing Sheets

UBIQUITIN-LYTIC PEPTIDE FUSION GENE CONSTRUCTS, PROTEIN PRODUCTS DERIVING THEREFROM, AND METHODS OF MAKING AND USING SAME

CROSS REFERENCE TO RELATED APPLICATIONS

This is a divisional of application Ser. No. 08/279,472, filed Jul. 22, 1994, now abandoned, which is a continuation-in-part of Application No. 08/231,730, filed April 20, 1994, now abandoned, in the names of Jesse M. Jaynes and Gordon R. Julian, which in turn is a continuation-in-part of Application No. 08/225,476, filed Apr. 8, 1994, now abandoned, in the names of Jesse M. Jaynes and Gordon R. Julian, which is in turn a continuation-in-part of Application No. 08/148,491, filed Nov. 8, 1993, now abandoned, and Application No. 08/148,889, filed Nov. 8, 1993, now abandoned, both filed in the name of Gordon R. Julian, which are in turn continuation-in-part of Application No. 08/039,620, filed Jun. 4, 1993, now abandoned, in the name of Jesse M. Jaynes and Gordon R. Julian.

BACKGROUND OF THE INVENTION

1. Field of the Invention

The present invention relates to ubiquitin-lytic peptide fusion gene constructs with enhanced stability and gene expression, ubiquitin-lytic peptide fusion protein products, and methods of making and using the same.

2. Description of Related Art

Naturally occurring lytic peptides play an important if not critical role as immunological agents in insects and have some, albeit secondary, defense functions in a range of other animals. The function of these peptides is to destroy procaryotic and other non-host cells by disrupting the cell membrane and promoting cell lysis. Common features of these naturally occurring lytic peptides include an overall basic charge, a small size (23–39 amino acid residues), and the ability to form amphipathic α-helices or β-pleated sheets. Several types of lytic peptides have been identified: cecropins (described in U.S. Pat. Nos. 4,355,104 and 4,520, 016 to Hultmark et al.), defensins, sarcotoxins, melittin, and magainins (described in U.S. Patent No. 4,810,777 to Zasloff). Each of these peptide types is distinguished by sequence and secondary structure characteristics.

Several hypotheses have been suggested for the mechanism of action of the lytic peptides: disruption of the membrane lipid bilayer by the anphipathic α-helix portion of the lytic peptide; lytic peptide formation of ion channels, which results in osmotically induced cytolysis; lytic peptide promotion of protein aggregation, which results in ion channel formation; and lytic peptide-induced release of phospholipids. Whatever the mechanism of lytic peptide-induced membrane damage, an ordered secondary conformation such as an amphipathic α-helix and positive charge density are features that appear to participate in the function of the lytic peptides.

Active synthetic analogs of naturally occurring lytic peptides have been produced and tested in vitro against a variety of procaryotic and eukaryotic cell types (see for example Arrowood, M. J., et al., J. Protozool. 38: 161s [199]; Jaynes, J. M., et al., FASEB J. 2: 2878 [1988]), including: gram positive and gram negative bacteria, fungi, yeast, protozoa, envelope viruses, virus-infected eukaryotic cells, and neoplastic or transformed mammalian cells. The results from these studies indicate that many of the synthetic lytic peptide analogs have similar or higher levels of lytic activity for many different types of cells, compared to the naturally occurring forms. In addition, the peptide concentration required to lyse microbial pathogens such as protozoans, yeast, and bacteria does not lyse normal mammalian cells. However, because previous work demonstrates that absolute sequence is not important as long as positive charge and amphipathy are preserved, the level of activity for a given synthetic peptide is difficult to predict.

The specificity of the lytic action also depends upon the concentration of the peptide and the type of membrane with which it interacts. Jaynes, J. M. et al., Peptide Research 2: 157 (1989) discuss the altered cytoskeletal characteristics of transformed or neoplastic mammalian cells that make them susceptible to lysis by the peptides. In these experiments, normal, human non-transformed cells remained unaffected at a given peptide concentration while transformed cells were lysed; however, when normal cells were treated with the cytoskeletal inhibitors cytochalasin D or colchicine, sensitivity to lysis increased. The experiments show that the action of lytic peptides on normal mammalian cells is limited. This resistance to lysis was most probably due to the well-developed cytoskeletal network of normal cells. In contrast, transformed cell lines which have well-known cytoskeletal deficiencies were sensitive to lysis. Because of differences in cellular sensitivity to lysis, lytic peptide concentration can be manipulated to effect lysis of one cell type but not another at the same locus.

Synthetic lytic peptide analogs can also act as agents of eukaryotic cell proliferation. Peptides that promote lysis of transformed cells will, at lower concentrations, promote cell proliferation in some cell types. This stimulatory activity is thought to depend on the channel-forming capability of the peptides, which somehow stimulates nutrient uptake, calcium influx or metabolite release, thereby stimulating cell proliferation (see Jaynes, J. M., Drug News & Perspectives 3: 69 [1990]; and Reed, W. A. et al., Molecular Reproduction and Development 31: 106 [1992]). Thus, at a given concentration, these peptides stimulate or create channels that can be beneficial to the normal mammalian cell in a benign environment where it is not important to exclude toxic compounds.

The synthetic lytic peptide analogs typically contain as few as 12 and as many as 40 amino acid residues. A phenylalanine residue is often positioned at the amino terminus of the protein to provide an aromatic moiety analogous to the tryptophan residue located near the amino terminus of natural cecropins and a UV-absorbing moiety with which to monitor the purification of the synthetic peptide. The basis for the design of these lytic peptide analogs is that a peptide of minimal length, having an amphipathic α-helical structural or a β-pleated sheet motif, and overall positive charge density effects lytic activity.

Plant disease is one of the leading causes of crop loss in the world and is estimated to cause up to one third of total crop loss worldwide; for example, in the potato losses associated with bacterial disease are as high as 25% of worldwide production. Additionally, the cultivation of a few species of plants in a concentrated area exacerbates the spread of disease. Recent advances in genetic engineering have lead to the development of plants with disease resistant phenotypes based on the expression of recombinant DNA molecules. Transgenic tobacco plants were engineered with both a wound inducible PiII promoter and a constitutive 35S promoter to express two lytic peptides (SHIVA-1 and SB-37) with bacteriolytic activity. The SHIVA-1 plant demonstrated enhanced resistance to bacterial wilt caused by infection by *Pseudomonas solanacearum* (Jaynes, J. M., et al., Plant Science 89: 43 (1993); Destefano-Beltran, L., et al., Biotechnology in Plant Disease Control, pp. 175–189, Wiley-Liss (1993). Thus lytic peptides have valuable uses as anti-phytopathogenic agents. However, chemical synthesis of these lytic peptides is very expensive. Therefore, alternate, more economical and efficient methods of synthesis are needed, such as in vivo synthesis in host cells using recombinant DNA methods.

Recombinant DNA molecules are produced by sub-cloning genes into plasmids using a bacterial host intermediate. In principle this technique is straightforward. However, any sequence that interferes with bacterial growth through replication or production of products toxic to the bacteria, such a lytic peptides, are difficult to clone. Often, host bacterial cells containing mutated forms of the DNA sequences encoding toxic products will be selected. These mutations can result in either decreased expression or production of an inactive product. Bacteria will even insert mutations that prevent expression of a potentially toxic product in cloned genes controlled by a eukaryotic promoter that is not active in prokaryotes. The effect of this selection of mutated species leads to an Inability to isolate sub-clones containing a non-mutated gene of choice. Thus, some sub-cloned genes are unstable in their bacterial hosts, although this instability can only be shown empirically. The bacteriolytic activity of the lytic peptides is an obstacle to the production of stable recombinant DNA molecules that express the genes at high levels.

For example, in an attempt to sub-clone into a standard plasmid vector a gene coding for frog magainin, a natural lytic peptide, bacterial transformants contained deletion mutations in the magainin coding region. Another attempt was made to sub-clone a synthetic lytic peptide (SEQ ID NO. 98) into a standard plasmid vector (pUC19) containing the Cauliflower Mosaic virus 35S promoter. The resulting transformants were screened by polymerase chain reaction (PCR). However, out of 30 colonies, only 2 sub-clones gave faint positive signals. These two sub-clones were sequenced. The sequence showed that one clone had a point mutation that introduced a stop codon ¾ of the way through the lytic peptide, and the other clone had a point mutation that changed the start codon from methionine to isoleucine. Both mutations would prevent the biosynthesis of the protein. Four more clones were analyzed, and of these four, one was sub-cloned an the wrong orientation, and three others had mutations introduced into the sequence. One of these sub-clones was selected for further analysis, but it inhibited the growth of its *E. coli* host. Thus, the production of recombinant DNA molecules coding for lytic peptides is difficult due to the uncertainty in obtaining the correct sub-clone.

Ubiquitin is a small, highly conserved protein present in all eukaryotes. Ubiquitins are encoded by gene families that are characterized by two types of basic structures. Polyubiquitin genes contain several direct repeats of ubiquitin, and ubiquitin-ribosomal fusion genes encode a single ubiquitin unit fused to the coding region for a small ribosomal associated protein. Both of these gene types are translated as polyproteins and then are processed By an endogenous ubiquitin hydrolase present in eukaryotes to release multiple ubiquitin proteins or ubiquitin and the ribosomal associated protein. A number of ubiquitin cDNAs or genomic clones have been isolated, including plant ubiquitin cDNAs and genomic clones from the potato (Garbarino, J. and Belknap, W., Plant Molecular Biology 24: 119 (1994); Garbarino. J. et al., Plant Molecular Biology 20: 235 (1992)).

U.S. Pat. Nos. 5,093,242 and 5,132,213 to Bachmair et al. teach the use of a ubiquitin cloning vector as a method of producing specified protein amino-termini. A recombinant DNA molecule was constructed with a protein coding gene fused at its amino terminus to a ubiquitin coding gene. Due to translation as a polypeptide and cleavage by hydrolases, a protein with any amino acid at the amino terminus can be generated. The amino terminus can be used to control the metabolic stability of the protein. However, the metabolic stability of the protein is dependent on the resulting amino acid at the amino-terminus, not the generation of a translation polypeptide.

The forgoing facts suggest that although lytic peptides as a class may include species that are efficacious in destroying bacteria, neoplastic cells, fungi, virus-infected cells, and protozoa, this lytic characteristic also decreases the stability of sub-cloned lytic peptides in host cells. This decreased stability hinders efforts to develop a more economical and efficient means of synthesizing lytic peptides.

It would therefore be a significant advance in the art, and is correspondingly an object of the present invention to develop a method of sub-cloning nucleotide sequences coding for lytic peptides into expression vectors, providing gene constructs with enhanced stability and gene expression and reduced toxicity.

SUMMARY OF THE INVENTION

The present invention relates generally to ubiquitin-lytic peptide fusion nucleic acid expression vectors comprising a promoter and ubiquitin polypeptide coding sequence ligated to a lytic peptide, ubiquitin-lytic peptide fusion protein products, and methods of making and using the same, as hereinafter more fully described.

It is another object of the invention to provide ubiquitin-lytic peptide fusion expression vectors and protein products derived therefrom.

It is another object of the invention to provide ubiquitin-lytic peptide fusion expression vectors that are expressed in plants having utility for promoting wound healing and combatting bacterial infections in plants.

It is a further object of this invention to provide ubiquitin-lytic peptide fusion polypeptides having utility for combatting protozoal infections, neoplasias, fungal infections, viral infections, and bacterial infections in mammals and plants.

It is yet another object of this invention to develop a method of sub-cloning polypeptide sequences in ubiquitin-fusion expression vectors with enhanced stability and gene expression.

It is yet another object of this invention to provide expression vectors containing constitutive and wound inducible ubiquitin promoters that are expressed in eukaryotic cells.

It is yet another object of this invention to provide expression vectors with procaryotic promoters that express ubiquitin-lytic peptide fusion genes in procaryotic hosts, the products of which can be cleaved in vitro by ubiquitin hydrolases.

These and other objects and advantages will be more fully apparent from the ensuing disclosure and claims.

DETAILED DESCRIPTION OF THE INVENTION AND PREFERRED EMBODIMENTS THEREOF

Figure 1:
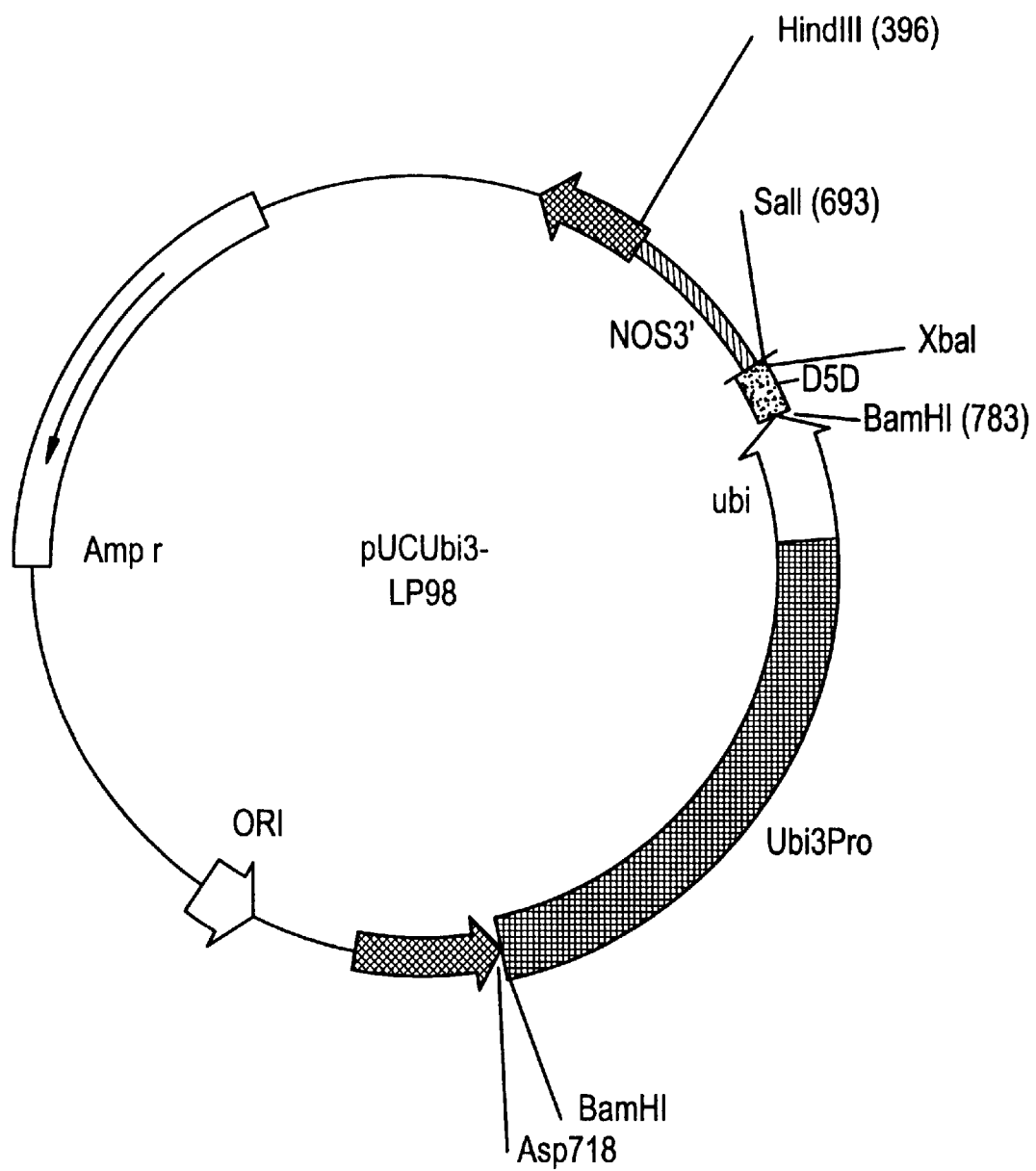
FIG. 1 is a map of a recombinant nucleic acid expression vector pUCUbi3-LP98 containing a 920 bp ubiquitin-ribosomal fusion gene promoter region linked to a 228 bp coding region for a ubiquitin polypeptide with a six bp BamHI site at the 3' end (SEQ ID NO. 93) that is fused at its 3' end to a gene coding for a lytic peptide (D5D*, SEQ ID NO. 98). The Ubi3 ubiquitin-lytic peptide nucleotide sequence corresponds to SEQ ID NO. 92. A nopaline synthase polyadenylation signal is located at the 3' end of the lytic peptide gene.

The disclosures of prior co-pending U.S. patent application No. 08/039,620 filed Jun. 4, 1993 in the names of Jesse M. Jaynes and Gordon R. Julian, U.S. patent application No. 08/148,889 filed Nov. 8, 1993 in the name of Gordon R. Julian, U.S. patent application No. 08/148,491 filed Nov. 8, 1993 in the name of Gordon R. Julian, U.S. patent application No. 08/225,476 filed Apr. 8, 1994 in the names of Jesse M. Jaynes and Gordon R.

Julian, and U.S. patent application No. 08/231,730 filed Apr. 20, 1994 in the names of Jesse M. Jaynes and Gordon R. Julian, are all hereby incorporated herein by reference in their entirety.

The term "amphipathic" as used herein refers to the distribution of hydrophobic and hydrophilic amino acid residues along opposing faces of an α-helix structure or other secondary conformation, which results in one face of the α-helix structure being predominantly hydrophobic and the other ace being predominantly hydrophilic. The degree of amphipathy of a peptide can be assessed by plotting the sequential amino acid residues on an Edmunson helical wheel (see also Kamtekar, S. et al., Science 262: 1680 (1993). The terms "peptide" and "polypeptide" as used herein refer to a molecule composed of a chain of amino acid residues and is intended to be construed as inclusive of polypeptides and peptides per se having molecular weights of up to 10,000 daltons, as well as proteins having molecular weights of greater that about 10,000 daltons, wherein the molecular weights are number average molecular weights. The term is also intended to be construed as inclusive of functional equivalents thereof when used in reference to a specific peptide coding sequence in the specification and claims herein. Functional equivalents of peptides and polypeptides include but are not limited to deletions, additions, and substitutions of amino acids in the polypeptide or peptide chain that do not adversely affect the overall function of the resulting peptide or polypeptide.

The term "plasmid" as used herein refers to a DNA molecule that is capable of autonomous replication within a host cell, either extrachromosomaily or as part of the host cell chromosome(s). The starting plasmids herein are commercially available, are publicly available on an unrestricted basis, or can be constructed from such available plasmids as disclosed herein and/or in accordance wish published procedures. In certain instances, as will be apparent to the ordinarily skilled artisan, other plasmids known in the art may be used interchangeable with plasmids described herein.

The term "ligation" as used herein refers to the process of forming phosphodiester bonds between two double-stranded DNA fragments. Unless otherwise specified, ligation is accomplished using standard procedures known to one skilled in the art.

The term "polymerase chain reaction," or "PCR" as used herein refers to a method for amplification of a desired nucleotide sequence in vitro, as described in U.S. Pat. No. 4,683,195, herein incorporated by reference in its entirety.

The term "nucleic acid" as used herein refers to deoxyribonucleic acid molecules (DNA) composed of a chain of deoxyribonucleotides and ribonucleic acid molecules (RNA) composed of a chain of ribonucleotides. The term "nucleic acid" as used herein is to be construed as including functional equivalents thereof when used in reference to a specific nucleotide sequence in the specification and claims herein. Functional equivalents of nucleic acid molecules include synonymous coding sequences with one or more codon substitutions and deletions or additions that do not effect the overall function of the resulting nucleic acid molecule. The degeneracy of the genetic code is well known to the art; therefore, synonymous coding sequences with one or more codon substitutions can be readily determined by one of ordinary skill in the art. Synonymous nucleotide coding sequences vary from the exemplified coding sequences but encode proteins of the same amino acid sequences as those specifically provided herein or proteins with similar function and are therefore also regarded as functional equivalents thereof.

The term "promoter" as used herein refers to an untranslated (i.e. one that does not result in a peptide or protein product) sequence upstream of the polypeptide coding region of a nucleotide sequence that controls transcription of a gene. Promoters typically fall into two classes, constitutive and inducible. Inducible promoters initiate high levels of transcription of the nucleic acid under their control in response to external stimuli. Constitutive promoters maintain a relatively constant level of transcription in a given cell. Suitable promoters for use in the present may include both procaryotic and eukaryotic promoters, with all ubiquitin promoters being preferred, solanaceous plant ubiquitin promoters being highly preferred, and potato ubiquitin promoters being most preferred. Additional control sequences such as ribosomal binding sites and enhancers may be included as control sequences when necessary.

The term "polyadenylation" sites as used herein refers to a control sequence located on the 3' end of a gene construct that provides a signal for cleavage and polyadenylation of the transcription unit expressed from the promoter. These control sequences are known to one skilled in the art The term "expression" as used herein refers to transcription and or translation of a nucleic acid sequence coding for a protein or peptide.

In one embodiment, the present invention is directed to an isolated nucleotide sequence comprising a gene coding for a ubiquitin polypeptide and functional equivalents thereof, linked to a ubiquitin promoter and functional equivalents thereof. Suitable ubiquitin promoters for use in the present invention include, but are not limited to, ubiquitin promoters from solanaceous plants. Preferably, the ubiquitin promoter is a potato plant ubiquitin promoter and most preferably it is the potato Ubi3 or Ubi7 promoter. In embodiments wherein the isolated nucleotide sequence codes for the potato Ubi3 promoter linked to a gene coding for a ubiquitin polypeptide it has a nucleotide sequence according to SEQ ID NO. 93. The Ubi3 promoter alone also has utility as constitutive promoter in eukaryotes.

In embodiments wherein the isolated nucleotide sequence codes for the potato Ubi7 promoter linked to a gene coding for a ubiquitin polypeptide it has a nucleotide sequence according to SEQ ID NO. 96. The Ubi7 nucleotide sequence according to SEQ ID NO. 96 includes an intron that is part of the ubiquitin transcription unit. The intron is not required for gene expression from the Ubi7 promoter, thus the Ubi7 promoter region without the intron can be considered as a specific functional equivalent of the Ubi7 promoter. The Ubi7 promoter alone, with or without the intron, has utility as a wound inducible promoter in eukaryotes.

Preferably, the nucleotide sequence comprising the isolated ubiquitin promoter and gene coding for a ubiquitin polypeptide further comprises a gene coding for a lytic peptide ligated to the 3' end of the gene coding for a ubiquitin polypeptide. Suitable genes coding for a lytic peptide have a nucleotide sequence coding for any one of the amino acid sequences according to SEQ ID NO. 1–91 and 97–98.

In one preferred embodiment, the present invention is directed to an isolated nucleotide sequence comprising a gene coding for a lytic peptide ligated to the 3' end of the gene coding for a ubiquitin polypeptide linked to the Ubi3 ubiquitin promoter having a nucleotide sequence according to SEQ ID NO. 92. In an alternative of this embodiment, the present invention is directed to an isolated nucleotide sequence comprising a gene coding for a lytic peptide ligated to the 3' end of the gene coding for a ubiquitin polypeptide linked to a Ubi7 ubiquitin promoter having a nucleotide sequence according to SEQ ID NO. 95.

In another embodiment, the present invention is directed to a recombinant nucleic acid expression vector. The vector is characterized in that it comprises a nucleotide sequence wherein a gene coding for a ubiquitin polypeptide is linked to a ubiquitin promoter. Preferably, the present invention is directed to a recombinant nucleic acid expression vector characterized in that it further comprises a nucleotide sequence wherein a gene coding for a lytic peptide is ligated to the 3' end of the gene coding for a ubiquitin polypeptide linked to a ubiquitin promoter. Suitable vectors for use in this invention include any eukaryotic or procaryotic expression vectors known in the art. Preferable vectors for use in this invention are pUC19 and pCGN1547.

In another embodiment, the present invention is directed to a host cell that is transformed by a recombinant DNA expression vector comprising a gene coding for a ubiquitin polypeptide linked to a ubiquitin promoter. Suitable host cells for transformation in the present invention include all known bacterial host cells, with all strains of *Escherichia coli* and *Agrobacterium tumefaciens* being preferred. Preferably, the present invention is directed to a host cell the recombinant DNA expression vector further comprises a gene coding for a lytic peptide ligated to the 3' end of the gene coding for a ubiquitin polypeptide linked to a ubiquitin promoter. Suitable genes coding for a lytic peptide have a nucleotide sequence coding for any one of the amino acid sequences according :to SEQ ID NO. 1–91 and 97–98.

Preferably, the present invention is directed to a solanaceous plant host cell that is transformed by a recombinant DNA expression vector. Most preferably the solanaceous plant cell is a potato plant host cell.

In another embodiment, the present invention is directed to an isolated nucleotide sequence and functional equivalents thereof coding for a lytic peptide, where the nucleotide sequence has a sequence coding for any one of the amino acid sequences according to SEQ ID NO. 1–91 and 97–98.

In yet another embodiment, the present invention is directed to a purified ubiquitin polypeptide and functional equivalents thereof having an amino acid sequence according to SEQ ID NO. 94. This embodiment can further comprise a lytic peptide translationally fused to the carboxy terminus of a ubiquitin polypeptide.

In another embodiment, the present invention is directed to a method of sub-cloning nucleotide sequences coding for lytic peptides and expressing such sequences in cells. The method comprises a first step wherein a recombinant nucleic acid containing a gene coding for a lytic peptide ligated to a gene coding for a ubiquitin polypeptide linked to a ubiquitin promoter is produced in a first host cell. Suitable first host cells include any known bacterial host cells. Preferably, the first host cell is either an *Escherichia coli* cell or an *Agrobacterium tumefaciens* cell.

If the peptides are sub-cloned using such a ubiquitin-fusion expression vector, the following advantage results: the lytic peptide gene constructs have increased stability in the bacterial host. While not wishing to be bound by any one theory, the present inventors believe that the stability is due to the ubiquitin protein coding nucleic acid region fused to the 5' end of the lytic peptide nucleic acid sequence. Bacteria do not contain the endogenous hydrolase necessary for cleavage of the ubiquitin fusion protein, so the gene constructs are not toxic to bacteria, since active lytic peptide cannot released. Thus functional equivalents of the ubiquitin fusion polypeptide include any ubiquitin molecule that is capable of deceiving the host cell into viewing the gene construct and its products as non-toxic.

In a variation of this embodiment, the recombinant nucleic acid vector is isolated from the first host cell and expressed in a second host cell. Suitable second host cells are plant and animal cells, preferably a solanaceous plant cell, and most preferably a potato plant cell. In the second host cell the fusion gene is expressed at high levels and the polyprotein is cleaved by endogenous ubiquitin hydrolases to produce active lytic peptide. These transgenic hosts provide from the expression vector lytic peptides in vivo to combat bacterial infections, fungal infections, protozoal infections, virus infections, and neoplasias. In addition, expression vectors containing ubiquitin promoters that are either constitutive or wound inducible are used to express peptides in eukaryotes.

The present invention is also directed to a method of sub-cloning nucleotide sequences coding for lytic peptides and expressing such sequences in cells. The method comprises producing in a host cell a recombinant nucleic acid expression vector comprising a gene coding for a lytic peptide ligated to the 3' end of a gene coding for a ubiquitin promoter linked to a procaryotic promoter sequence. Suitable procaryotic promoters include those known to one skilled in the art to be active in prokaryotes and used in plasmid vectors for bacterial gene expression.

The recombinant nucleic acid expression vector is expressed in the host cell and ubiquitin-lytic peptide fusion polypeptides are isolated from the host. Preferably, the host cell is either an *Escherichia coli* cell or an *Agrobacterium tumefaciens* cell. The isolated ubiquitin-lytic peptide fusion polypeptides are then cleaved in vitro by ubiquitin hydrolases to release the lytic peptides from the ubiquitin polypeptide (see U.S. Pat. No. 5,196,321 to Bachmair et al.). The active lytic peptides are then used to treat bacterial infections, fungal infections, protozoal infections, virus infections, and neoplasias. These isolated lytic peptides are in some instances glyoxylated or methylated in vitro to stabilize against proteolytic digestion in vivo.

Ubiquitin fusion expression vectors thus have broad utility as cloning and expression vectors to stabilize and sub-clone lytic peptides nucleotide sequences, as well as a wide variety of protein coding nucleic acid sequences that are otherwise toxic to their hosts. The ubiquitin-lytic peptide expression vectors also have broad utility as an economical and efficient means to synthesize lytic peptides in host cells. These lytic peptides have utility for combatting protozoal infections, neoplasias, fungal infections, viral infections, and bacterial infections in mammals and plants.

The features and advantages of the invention are more fully shown by the following illustrative examples and embodiments, which are not to be limitingly construed as regard the broad scope, utility, and applicability of the invention.

EXAMPLE 1

Representative Lytic Peptides and Ubiquitin Polypeptide

Set out in Table 1 below as illustrative examples of lytic peptides are the amino acid sequences of families of related lytic peptides. These lytic peptides are designated for ease of reference as SEQ ID NO. 1–91 and 97–98. Nucleic acid sequences coding for these lytic peptides and functional equivalents thereof represent examples of lytic peptide nucleic acid sequences that are sub-cloned to make ubiquitin-lytic peptide fusion gene constructs and polypeptides. The ubiquitin polypeptide, designated for ease of reference as SEQ ID NO. 94, and functional equivalents thereof, represents an example of the 5' fusion ubiquitin polypeptide.

TABLE 1

LYTIC PEPTIDE SEQUENCES

SEQ ID NO. 1

Phe Ala Val Ala Val Lys Ala Val Lys Lys Ala Val Lys Val Lys
1             5                 10                15
Lys Ala Val Lys Lys Ala Val Lys Lys Lys
              20                25

SEQ ID NO. 2

Phe Ala Val Ala Val Lys Ala Val Ala Val Lys Ala Val Lys Lys Ala
1             5                 10                15
Val Lys Lys Val Lys Lys Ala Val Lys Lys Ala Val Lys Lys Lys
              20                25                30

SEQ ID NO. 3

Phe Ala Val Ala Val Lys Ala Val Ala Val L

TABLE 1-continued

LYTIC PEPTIDE SEQUENCES

SEQ ID NO. 4

Phe Ala Val Ala Val Lys Ala Val Lys Lys Ala Val Lys Val Lys
1               5                   10                  15
Lys Ala Val Lys Lys Ala Val
            20

SEQ ID NO. 5

Phe Ala Val Ala Val Lys Ala Val Ala Val Lys Ala Val Lys Lys Ala
1               5                   10                  15
Val Lys Lys Val Lys Ala Val Lys Lys Ala Val
            20                  25

SEQ ID NO. 6

Phe Ala Val Ala Val Lys Ala Val Ala Val Lys Ala Val Ala Val Lys
1               5                   10                  15
Ala Val Lys Lys Ala Val Lys Lys Val Lys Lys Ala Val Lys Lys Ala
            20                  25                  30
Val

SEQ ID NO. 7

Phe Ala Val Gly Leu Arg Ala Ile Lys Arg Ala Leu Lys Lys Leu Arg
1               5                   10                  15
Arg Gly Val Arg Lys Val Ala Lys Arg Lys Arg
            20                  25

SEQ ID NO. 8

Phe Ala Val Gly Leu Arg Ala Ile Lys Arg Ala Leu Lys Lys Leu Arg
1               5                   10                  15
Arg Gly Val Arg Lys Val Ala
            20

SEQ ID NO. 9

Lys Arg Lys Arg Ala Val Lys Arg Val Gly Arg Arg Leu Lys Lys Leu
1               5                   10                  15
Ala Arg Lys Ile Ala Arg Leu Gly Val Ala Phe
            20                  25

SEQ ID NO. 10

Ala Val Lys Arg Val Gly Arg Arg Leu Lys Lys Leu Ala Arg Lys Ile
1               5                   10                  15
Ala Arg Leu Gly Val Ala Phe
            20

SEQ ID NO. 11

Phe Ala Val Gly Leu Arg Ala Ile Lys Arg Ala Leu Lys Lys Leu Arg
1               5                   10                  15
Arg Gly Val Arg Lys Val Ala Lys Arg Lys Arg Lys Lys Asp Leu
            20                  25                  30

SEQ ID NO. 12

Phe Ala Val Gly Leu Arg Ala Ile Lys Arg Ala Leu Lys Lys Leu Arg
1               5                   10                  15
Arg Gly Val Arg Lys Val Ala Lys Asp Leu
            20                  25

SEQ ID NO. 13

Lys Arg Lys Arg Ala Val Lys Arg Val Gly Arg Arg Leu Lys Lys Leu
1               5                   10                  15
Ala Arg Lys Ile Ala Arg Leu Gly Val Ala Phe Lys Asp Leu
            20                  25                  30

SEQ ID NO. 14

Ala Val Lys Arg Val Gly Arg Arg Leu Lys Lys Leu Ala Arg Lys Ile
1               5                   10                  15

TABLE 1-continued

LYTIC PEPTIDE SEQUENCES

Ala Arg Leu Gly Val Ala Phe Lys Asp Leu
           20           25

SEQ ID NO. 15

Lys Lys Lys Lys Phe Val Lys Lys Val Ala Lys Val Lys Lys Val
1            5             10            15
Ala Lys Lys Val Ala Lys Val Ala Val Ala Val
         20           25

SEQ ID NO. 16

Lys Lys Lys Lys Phe Val Lys Lys Val Ala Lys Val Lys Lys Val
1            5             10            15
Ala Lys Lys Val Ala Lys Val Ala Val Ala Lys Val Ala Val Ala Val
         20           25           30

SEQ ID NO. 17

Lys Lys Lys Lys Phe Val Lys Lys Val Ala Lys Val Lys Lys Val
1            5             10            15
Ala Lys Lys Val Ala Lys Val Ala Val Ala Lys Val Ala Val Ala Lys
         20           25           30
Val Ala Val Ala Val
         35

SEQ ID NO. 18

Phe Val Lys Lys Val Ala Lys Lys Val Lys Val Ala Lys Lys Val
1            5             10            15
Ala Lys Val Ala Val Ala Val
         20

SEQ ID NO. 19

Phe Val Lys Lys Val Ala Lys Lys Val Lys Val Ala Lys Lys Val
1            5             10            15
Ala Lys Val Ala Val Ala Lys Val Ala Val Ala Val
         20           25

SEQ ID NO. 20

Phe Val Lys Lys Val Ala Lys Lys Val Lys Val Ala Lys Lys Val
1            5             10            15
Ala Lys Val Ala Val Ala Lys Val Ala Val Ala Lys Val Ala Val Ala
         20           25           30
Val

SEQ ID NO. 21

Lys Lys Lys Lys Phe Val Lys Val Ala Lys Val Ala Lys Lys Val
1            5             10            15
Ala Lys Val Ala Lys Lys Val Ala Lys Lys Val
         20           25

SEQ ID NO. 22

Lys Lys Lys Lys Phe Val Lys Lys Val Ala Val Ala Lys Lys Val
1            5             10            15
Ala Lys Val Ala Lys Lys Val Ala Lys Lys Val Ala Lys Lys Val Ala
         20           25           30

SEQ ID NO. 23

Lys Lys Lys Lys Phe Val Lys Lys Val Ala Val Ala Lys Lys Val
1            5             10            15
Ala Lys Val Ala Lys Lys Val Ala Lys Lys Val Ala Lys Lys Val Ala
         20           25           30
Lys Val Ala Lys Lys
         35

SEQ ID NO. 24

Phe Val Lys Lys Val Ala Lys Val Ala Lys Val Ala Lys Val Ala
1            5             10            15
Lys Lys Val Ala Lys Lys Val
         20

TABLE 1-continued

LYTIC PEPTIDE SEQUENCES

SEQ ID NO. 25

Phe Val Lys Lys Val Ala Lys Val Ala Lys Lys Val Ala Lys Val Ala
1               5                   10                  15
Lys Lys Val Ala Lys Val Ala Lys Lys Val Ala
            20                  25

SEQ ID NO. 26

Phe Val Lys Lys Val Ala Lys Val Ala Lys Lys Val Ala Lys Val Ala
1               5                   10                  15
Lys Lys Val Ala Lys Val Ala Lys Lys Val Ala Lys Val Ala Lys
            20                  25                  30
Lys

SEQ ID NO. 27

Phe Val Lys Lys Val Ala Lys Val Ala Lys Lys Val Ala Lys Val Ala
1               5                   10                  15
Lys Lys Val Ala Lys Val Lys Lys Lys Lys
            20                  25

SEQ ID NO. 28

Phe Val Lys Lys Val Ala Lys Val Ala Lys Lys Val Ala Lys Val Ala
1               5                   10                  15
Lys Lys Val Ala Lys Val Ala Lys Lys Val Ala Lys Lys Lys Lys
            20                  25                  30

SEQ ID NO. 29

Phe Val Lys Lys Val Ala Lys Val Ala Lys Lys Val Ala Lys Val Ala
1               5                   10                  15
Lys Lys Val Ala Lys Val Ala Lys Lys Val Ala Lys Val Ala Lys
            20                  25                  30
Lys Lys Lys Lys
        35

SEQ ID NO. 30

Phe Lys Val Lys Ala Lys Val Lys Ala Lys Val Lys Lys Lys Lys
1               5                   10                  15

SEQ ID NO. 31

Phe Lys Val Lys Ala Lys Val Lys Ala Lys Val Lys Ala Lys Val Lys
1               5                   10                  15
Ala Lys Lys Lys Lys
            20

SEQ ID NO. 32

Phe Lys Val Lys Ala Lys Val Lys Ala Lys Val Lys Ala Lys Val Lys
1               5                   10                  15
Ala Lys Val Lys Ala Lys Val Lys Lys Lys Lys
            20                  25

SEQ ID NO. 33

Phe Lys Val Lys Ala Lys Val Lys Ala Lys Val Lys
1               5                   10

SEQ ID NO. 34

Phe Lys Val Lys Ala Lys Val Lys Ala Lys Val Lys Ala Lys Val Lys
1               5                   10                  15
Ala

SEQ ID NO. 35

Phe Lys Val Lys Ala Lys Val Lys Ala Lys Val Lys Ala Lys Val Lys
1               5                   10                  15
Ala Lys Val Lys Ala Lys Val

TABLE 1-continued

LYTIC PEPTIDE SEQUENCES

20

SEQ ID NO. 36

Lys Lys Lys Lys Phe Lys Val Lys Ala Lys Val Lys Ala Lys Val Lys
1               5                   10                  15

SEQ ID NO. 37

Lys Lys Lys Lys Phe Lys Val Lys Ala Lys Val Lys Ala Lys Val Lys
1               5                   10                  15
Ala Lys Val Lys Ala
            20

SEQ ID NO. 38

Lys Lys Lys Lys Phe Lys Val Lys Ala Lys Val Lys Ala Lys Val Lys
1               5                   10                  15
Ala Lys Val Lys Ala Lys Val Lys Ala Lys Val
            20                  25

SEQ ID NO. 39

Phe Lys Lys Val Lys Lys Val Ala Lys Lys Val Cys Lys Cys Val Lys
1               5                   10                  15
Lys Ala Val Lys Lys Val'Lys Lys Phe
            20                  25

SEQ ID NO. 40

Phe Ala Val Ala Val Lys Ala Val Lys Lys Ala Val Lys Lys Val Lys
1               5                   10                  15
Lys Ala Val Lys Lys Ala Val Cys Cys Cys Cys
            20                  25

SEQ ID NO. 41

Cys Cys Cys Cys Phe Val Lys Lys Val Ala Lys Lys Val Lys Lys Val
1               5                   10                  15
Ala Lys Lys Val Ala Lys Val Ala Val Ala Val
            20                  25

SEQ ID NO. 42

Phe Ala Val Ala Val Lys Ala Val Lys Lys Ala Val Lys Lys Val Lys
1               5                   10                  15
Lys Ala Val Lys Lys Ala Val Ser Ser Ser Ser
            20                  25

SEQ ID NO. 43

Ser Ser Ser Ser Phe Val Lys Lys Val Ala Lys Lys Val Lys Lys Val
1               5                   10                  15
Ala Lys Lys Val Ala Lys Val Ala Val Ala Val
            20                  25

SEQ ID NO. 44

Phe Ala Leu Ala Leu Lys Ala Leu Lys Lys Ala Leu Lys Lys Leu Lys
1               5                   10                  15
Lys Ala Leu Lys Lys Ala Leu
            20

SEQ ID NO. 45

Leu Ala Lys Lys Leu Ala Lys Leu Lys Lys Leu Ala Lys Lys Lys Leu
1               5                   10                  15
Ala Lys Leu Ala Leu Ala Phe
            20

SEQ ID NO. 46

Phe Ala Phe Ala Phe Lys Ala Phe Lys Lys Ala Phe Lys Lys Phe Lys
1               5                   10                  15
Lys Ala Phe Lys Lys Ala Phe
            20

TABLE 1-continued

LYTIC PEPTIDE SEQUENCES

SEQ ID NO. 47

Phe Ala Ile Ala Ile Lys Ala Ile Lys Lys Ala Ile Lys Lys Ile Lys
1               5                   10                  15
Lys Ala Ile Lys Lys Ile
            20

SEQ ID NO. 48

Phe Ala Lys Lys Phe Ala Lys Lys Phe Lys Lys Phe Ala Lys Lys Phe
1               5                   10                  15
Ala Lys Phe Ala Phe Ala Phe
            20

SEQ ID NO. 49

Phe Lys Arg Leu Ala Lys Ile Lys Val Leu Arg Leu Ala Lys Ile Lys
1               5                   10                  15
Arg

SEQ ID NO. 50

Lys Leu Lys Leu Ala Val Lys Leu Val Gly Leu Leu Arg Lys Lys Arg
1               5                   10                  15
Ala Leu Lys Ile Ala Leu Arg Gly Val Ala Lys Arg Ala Gly Arg Leu
            20                  25                  30
Ala Val Arg Lys Phe
        35

SEQ ID NO. 51

Phe Ala Arg Ala Arg Lys Ala Arg Lys Lys Ala Arg Lys Lys Arg Lys
1               5                   10                  15
Lys Ala Arg Lys Ala Arg Lys Asp Arg
            20                  25

SEQ ID NO. 52

Phe Ala Val Ala Val Cys Ala Val Cys Cys Ala Val Cys Cys Val Cys
1               5                   10                  15
Cys Ala Val Cys Cys Ala Val
            20

SEQ ID NO. 53

Phe Ala Val Ala Val Ser Ala Val Ser Ser Ala Val Ser Ser Val Ser
1               5                   10                  15
Ser Ala Val Ser Ser Ala Val
            20

SEQ ID NO. 54

Phe Ala Val Ala Val Ser Ala Val Ser Ser Ala Val Ser Ser Val Ser
1               5                   10                  15
Ser Ala Val Ser Ser Ala Val Ser Ser Ser
            20                  25

SEQ ID NO. 55

Phe Ala Lys Lys Phe Ala Lys Lys Phe Lys Lys Phe Ala Lys Lys Phe
1               5                   10                  15
Ala Lys Phe Ala Phe Ala Phe Lys Lys Lys Lys
            20                  25

SEQ ID NO. 56

Lys Lys Lys Lys Phe Ala Lys Lys Phe Ala Lys Lys Phe Lys Lys Phe
1               5                   10                  15
Ala Lys Lys Phe Ala Lys Phe Ala Phe Ala Phe
            20                  25

SEQ ID NO. 57

Phe Ala Arg Lys Phe Leu Lys Arg Phe Lys Lys Phe Val Arg Lys Phe
1               5                   10                  15
Ile Arg Phe Ala Phe Leu Phe
            20

TABLE 1-continued

LYTIC PEPTIDE SEQUENCES

SEQ ID NO. 58

Phe Ala Arg Lys Phe Leu Lys Arg Phe Lys Lys Phe Val Arg Lys Phe
1               5                   10                  15
Ile Arg Phe Ala Phe Leu Phe Lys Arg Lys Arg
            20              25

SEQ ID NO. 59

Lys Arg Lys Arg Phe Ala Arg Lys Phe Leu Lys Arg Phe Lys Lys Phe
1               5                   10                  15
Val Arg Lys Phe Ile Arg Phe Ala Phe Leu Phe
            20              25

SEQ ID NO. 60

Ile Ala Lys Lys Ile Ala Lys Lys Ile Lys Lys Ile Ala Lys Lys Ile
1               5                   10                  15
Ala Lys Ile Ala Ile Ala Ile
            20

SEQ ID NO. 61

Ile Ala Lys Lys Ile Ala Lys Lys Ile Lys Lys Ile Ala Lys Lys Ile
1               5                   10                  15
Ala Lys Ile Ala Ile Ala Ile Lys Lys Lys
            20              25

SEQ ID NO. 62

Lys Lys Lys Lys Ile Ala Lys Lys Ile Ala Lys Lys Ile Lys Lys Ile
1               5                   10                  15
Ala Lys Lys Ile Ala Lys Ile Ala Ile Ala Ile
            20              25

SEQ ID NO. 63

Ile Ala Arg Lys Ile Leu Lys Arg Ile Lys Lys Ile Val Arg Lys Phe
1               5                   10                  15
Ile Arg Ile Ala Ile Leu Ile
            20

SEQ ID NO. 64

Ile Ala Arg Lys Ile Leu Lys Arg Ile Lys Lys Ile Val Arg Lys Phe
1               5                   10                  15
Ile Arg Ile Ala Ile Leu Ile Lys Arg Lys Arg
            20              25

SEQ ID NO. 65

Lys Arg Lys Arg Ile Ala Arg Lys Ile Leu Lys Arg Ile Lys Lys Ile
1               5                   10                  15
Val Arg Lys Phe Ile Arg Ile Ala Ile Leu Ile
            20              25

SEQ ID NO. 66

Phe Lys Leu Arg Ala Lys Ile Lys Val Arg Leu Arg Ala Lys Ile Lys
1               5                   10                  15
Leu

SEQ ID NO. 67

Lys Arg Lys Arg Phe Lys Leu Arg Ala Lys Ile Lys Val Arg Leu Arg
1               5                   10                  15
Ala Lys Ile Lys Leu
            20

SEQ ID NO. 68

Phe Lys Leu Arg Ala Lys Ile Lys Val Arg Leu Arg Ala Lys Ile Lys
1               5                   10                  15
Leu Lys Arg Lys Arg
            20

TABLE 1-continued

LYTIC PEPTIDE SEQUENCES

SEQ ID NO. 69

Phe Lys Leu Arg Ala Lys Ile Lys Val Arg Leu Arg Ala Lys Ile Lys
1               5                   10                  15
Leu Arg Val Lys Leu Lys Ile
            20

SEQ ID NO. 70

Phe Lys Leu Arg Ala Lys Ile Lys Val Arg Leu Arg Ala Lys Ile Lys
1               5                   10                  15
Leu Arg Val Lys Leu Lys Ile Lys Arg Lys Arg
            20                  25

SEQ ID NO. 71

Lys Arg Lys Arg Phe Lys Leu Arg Ala Lys Ile Lys Val Arg Leu Arg
1               5                   10                  15
Ala Lys Ile Lys Leu Arg Val Lys Leu Lys Ile
            20                  25

SEQ ID NO. 72

Phe Lys Leu Arg Ala Lys Ile Lys Val Arg Leu Arg Ala Lys Ile Lys
1               5                   10                  15
Leu Arg Val Lys Leu Lys Ile Arg Ala Arg Ile Lys Leu
            20                  25

SEQ ID NO. 73

Phe Lys Leu Arg Ala Lys Ile Lys Val Arg Leu Arg Ala Lys Ile Lys
1               5                   10                  15
Leu Arg Val Lys Leu Lys Ile Arg Ala Arg Ile Lys Leu Lys Arg Lys
            20                  25                  30
Arg

SEQ ID NO. 74

Lys Arg Lys Arg Phe Lys Leu Arg Ala Lys Ile Lys Val Arg Leu Arg
1               5                   10                  15
Ala Lys Ile Lys Leu Arg Val Lys Leu Lys Ile Arg Ala Arg Ile Lys
            20                  25                  30
Leu

SEQ ID NO. 75

Phe Lys Leu Arg Ala Lys Ile Lys Val Arg Leu Arg Ala Lys Ile Lys
1               5                   10                  15
Leu Val Phe Ala Ile Leu Leu
            20

SEQ ID NO. 76

Phe Lys Leu Arg Ala Lys Ile Lys Val Arg Leu Arg Ala Lys Ile Lys
1               5                   10                  15
Leu Val Phe Ala Ile Leu Leu Lys Arg Lys Arg
            20                  25

SEQ ID NO. 77

Lys Arg Lys Arg Phe Lys Leu Arg Ala Lys Ile Lys Val Arg Leu Arg
1               5                   10                  15
Ala Lys Ile Lys Leu Val Phe Ala Ile Leu Leu
            20                  25

SEQ ID NO. 78

Val Phe Ala Ile Leu Leu Phe Lys Leu Arg Ala Lys Ile Lys Val Arg
1               5                   10                  15
Leu Arg Ala Lys Ile Lys Leu
            20

SEQ ID NO. 79

Val Phe Ala Ile Leu Leu Phe Lys Leu Arg Ala Lys Ile Lys Val Arg
1               5                   10                  15
Leu Arg Ala Lys Ile Lys Leu Arg Lys Arg

TABLE 1-continued
LYTIC PEPTIDE SEQUENCES

SEQ ID NO. 80

Lys Arg Lys Arg Val Phe Ala Ile Leu Leu Phe Lys Leu Arg Ala Lys
1               5                   10                  15
Ile Lys Val Arg Leu Arg Ala Lys Ile Lys Leu
            20                  25

SEQ ID NO. 81

Val Gly Glu Cys Val Arg Gly Arg Cys Pro Ser Gly Met Cys Cys Ser
1               5                   10                  15
Gln Phe Gly Tyr Cys Gly Lys Gly Pro Lys Tyr Cys Gly
            20                  25

SEQ ID NO. 82

Val Gly Glu Cys Val Arg Gly Arg Cys Pro Ser Gly Met Cys Cys Ser
1               5                   10                  15
Gln Phe Gly Tyr Cys Gly Lys Gly Pro Lys Tyr Cys Gly Arg
            20                  25                  30

SEQ ID NO. 83

Leu Gly Asp Cys Leu Lys Gly Lys Cys Pro Ser Gly Met Cys Cys Ser
1               5                   10                  15
Asn Tyr Gly Phe Cys Gly Arg Gly Pro Arg Phe Cys Gly Lys
            20                  25                  30

SEQ ID NO. 84

Gln Cys Ile Gly Asn Gly Gly Arg Cys Asn Glu Asn Val Gly Pro Pro
1               5                   10                  15
Tyr Cys Cys Ser Gly Phe Cys Leu Arg Gln Pro Gly Gln Gly Tyr Gly
            20                  25                  30
Tyr Cys Lys Asn Arg
        35

SEQ ID NO. 85

Cys Ile Gly Asn Gly Gly Arg Cys Asn Glu Asn Val Gly Pro Pro Tyr
1               5                   10                  15
Cys Cys Ser Gly Phe Cys Leu Arg Gln Pro Asn Gln Gly Tyr Gly Val
            20                  25                  30
Cys Arg Asn Arg
        35

SEQ ID NO. 86

Cys Ile Gly Gln Gly Gly Lys Cys Gln Asp Gln Leu Gly Pro Pro Phe
1               5                   10                  15
Cys Cys Ser Gly Tyr Cys Val Lys Asn Pro Gln Asn Gly Phe Gly Leu
            20                  25                  30
Cys Lys Gln Lys
        35

SEQ ID NO. 87

Gln Lys Leu Cys Glu Arg Pro Ser Gly Thr Trp Ser Gly Val Cys Gly
1               5                   10                  15
Asn Asn Asn Ala Cys Lys Asn Gln Cys Ile Asn Leu Glu Lys Ala Arg
            20                  25                  30
His Gly Ser Cys Asn Tyr Val Phe Pro Ala His Lys
        35                  40

SEQ ID NO. 88

Gln Arg Val Cys Asp Lys Pro Ser Gly Thr Trp Ser Gly Leu Cys Gly
1               5                   10                  15
Asn Asn Asn Ala Cys Arg Gln Asn Cys Ile Gln Val Asp Arg Ala Lys
            20                  25                  30
Lys Gly Ser Cys Gln Phe Leu Tyr Pro Ala Lys Lys
        35                  40

SEQ ID NO. 89

TABLE 1-continued
LYTIC PEPTIDE SEQUENCES

Gln Lys Leu Cys Gln Arg Pro Ser Gly Thr Trp Ser Gly Val Cys Gly
1               5                   10                  15
Asn Asn Asn Ala Cys Lys Asn Gln Cys Ile Arg Leu Glu Lys Ala Arg
            20                  25                  30
His Gly Ser Cys
            35

SEQ ID NO. 90

Gln Arg Val Cys Asn Lys Pro Ser Gly Thr Trp Ser Gly Leu Cys Gly
1               5                   10                  15
Asn Asn Asn Ala Cys Arg Gln Asn Cys Ile Lys Val Asp Arg Ala Lys
            20                  25                  30
Lys Gly Ser Cys
            35

SEQ ID NO. 91

Met Leu Glu Glu Leu Phe Glu Glu Met Thr Glu Phe Ile Glu Glu Val
1               5                   10                  15
Ile Glu Thr Met
            20

SEQ ID NO. 94

Met Gln Ile Phe Val Lys Thr Leu
1               5
Thr Gly Lys Thr Ile Thr Leu Glu Val Glu Ser Ser Asp Thr
        10              15                  20
Ile Asp Asn Val Lys Ala Lys Ile Gln Asp Lys Glu Gly Ile
            25                  30                  35
Pro Pro Asp Gln Gln Arg Leu Ile Phe Ala Gly Lys Gln Leu
                40                  45                  50
Glu Asp Gly Arg Thr Leu Ala Asp Tyr Asn Ile Gln Lys Glu
                    55                  60
Ser Thr Leu His Leu Val Leu Arg Leu Arg Gly Gly Ser
65                      70                  75

SEQ ID NO. 97

Lys Arg Lys Arg Ala Val Lys Arg Val Gly Arg Arg Leu Lys Lys Leu
1               5                   10                  15
Ala Arg Lys Ile Ala Arg Leu Gly Val Ala Lys Leu Ala Gly Leu Arg
            20                  25                  30
Ala Val Leu Lys Phe
            35

SEQ ID NO. 98

Ala Val Lys Arg Val Gly Arg Arg Leu Lys Lys Leu Asp Arg Lys Ile
1               5                   10                  15
Asp Arg Leu Gly Val Asp Phe
            20

EXAMPLE 2

Construction of Ubiquitin-Lytic Peptide Fusion Plasmids With Ubiquitin-ribosomal Fusion Gene Promoter (Ubi3)

Exemplary and preferred pUC19 and pCGN1547 plasmid vectors containing a potato (*Solanum tuberosum*) ubiquitin-ribosomal fusion promoter (Ubi3), a region coding for a ubiquitin polypeptide, and a gene coding for a lytic peptide are constructed.

To obtain the genomic clone containing a ubiquitin-ribosomal fusion promoter and ubiquitin polypeptide coding region, a αFIXII potato genomic library is first prescreened using PCR. The PCR primers are homologous to regions of the ubiquitin-ribosomal fusion cDNA (see Garbarino J., et al., Plant Molecular Biology 20: 235(1992); Garbarino J. and Belknap W., Plant Molecular Biology 30 24: 119 (1994); both of which are hereby incorporated by reference herein in their entirety). A primer 5' to the beginning ATG of ubiquitin and a primer complementary to a sequence near the 5' end of the ribosomal protein are used.

The library is plated in 22 aliquots containing approximately $0.5 \times 10^6$ pfu (plaque forming units) each on an *E. coli* lawn. A plug is taken from each of the 22 resulting plaques and the eluant from each is subjected to PCR under standard conditions. The PCR products are run on agarose gels. The gels are then blotted and probed with the ubiquitin coding region of the ubiquitin-ribosomal fusion cDNA according to standard conditions. Two of the plugs produce PCR products that hybridize to the cDNA probe., Both of these are the correct size for the predicted ubiquitin-ribosomal fusion genomic fragment.

The eluants from these two plugs are then plated and screened with the ubiquitin coding region of the ubiquitin-ribosomal fusion cDNA according to standard conditions. For verification, the positive plaques from the initial screen are replated and screened with a probe containing both the ribosomal protein-coding region and the 3' end of the potato ubiquitin-ribosomal fusion cDNA.

The genomic clones are sequenced using Sequenase version 2.0 15 (United States Biochemical Corporation) or Promega fmol DNA Sequencing System using standard conditions. A genomic clone containing both the ubiquitin-ribosomal fusion promoter region and the ubiquitin-ribosomal fusion coding region is identified.

A chimeric gene is then constructed with a portion of the potato ubiquitin-ribosomal fusion genomic clone ligated to a lytic peptide gene. PCR is used to generate the Ubi3 promoter and ubiquitin portion of the chimeric gene. The Ubi3 promoter region includes the 920 bp promoter region upstream of the ubiquitin ATG, and the ubiquitin polypeptide coding region is 228 bp plus 6 bp of a BamHI restriction site at the 3' end (SEQ ID NO. 93). The primers contain BamHI restriction sites and are homologous to the 5' end of the Ubi3 promoter and to the 3' end of the ubiquitin polypeptide coding region. The ubiquitin-ribosomal fusion genomic clone is used as the amplification template. This insert is first sub-cloned into she plasmid pCGN1547, as described in Garbarino et al., Plant Molecular Biology 24: 119 (1994). The Ubi3 insert is then isolated from pCGN1547 using the BamHI sites and ligated into pUC19 under standard conditions. Transformation of E. coli is done according to standard conditions and correct sub-clones are confirmed by mini-prep or PCR DNA analysis. This plasmid is designated pUCUbi3.

A nucleotide fragment coding for the lytic peptide (corresponding to the amino acid sequence SEQ ID NO. 98) is synthesized using a nucleic acid synthesizer, adding a stop codon to the 3' end, and used as a PCR template. The 5' PCR primer homologous to the lytic peptide nucleotide sequence contains a BamHI site, and the 3' primer contains an XbaI site. These sites are used to sub-clone the PCR generated insert into pUC19. A nopaline synthase polyadenylation signal (NOS3') is then cloned 3' to the lytic peptide sequence. Following sequence analysis, the BamHI insert containing the Ubi3 promoter and ubiquitin coding region (SEQ ID NO. 93) is cloned 5' to the lytic peptide.

After transforming E. coli under standard conditions, pUC19 sub-clones are selected for mini-prep or PCR DNA analysis according to standard conditions. The direction of the promoter is confirmed and the junction sequences are verified by sequencing according to standard conditions. The resulting Ubi3 ubiquitin-lytic peptide fusion gene construct corresponds to SEQ ID NO. 92. Unlike previous cloning attempts using the CaMV35S promoter, as described in the Background section, the sequence does not reveal any point mutations in the lytic peptide sub-clones. The plasmid is stable in the E. coli host and did not inhibit its growth.

The resulting pUC19 recombinant plasmid is shown in the plasmid map in FIG. 1. The sequence for the Ubi3-ubiquitin insert containing the ubiquitin-ribosomal fusion gene promoter and the ubiquitin coding region corresponds to SEQ ID NO. 93 in Table 2 below. The sequence for the chimeric Ubi3 ubiquitin-lytic peptide fusion gene construct corresponds to SEQ ID NO. 92 in Table 2 below. This plasmid is designated as pUCUbi3-LP98.

The entire Ubi3 ubiquitin-lytic peptide fusion gene construct, including the polyadenylation site, was isolated from pUC19 as an Asp718/HindIII restriction fragment and sub-cloned into the pCGN1547 Agrobacterium vector for use in plant transformation (see McBride, et al., Plant Molecular Biology 14:269 (1990). This plasmid is designated as pCGNUbi3-LP98.

TABLE 2

NUCLEOTIDE SEQUENCE OF POTATO UBIQUITIN-RIBOSOMAL
FUSION PROMOTER (UBI3) AND UBIQUITIN CODING REGION
INSERT, AND UBIQUITIN-LYTIC PEPTIDE FUSION GENE CONSTRUCT

SEQ ID NO. 92

| | | | | |
|---|---|---|---|---|
| CCAAAGCACA | TACTTATCGA | TTTAAATTTC | ATCGAAGAGA | TTAATATCGA | 50 |
| ATAATCATAT | ACATACTTTA | AATACATAAC | AAATTTTAAA | TACATATATC | 100 |
| TGGTATATAA | TTAATTTTTT | AAAGTCATGA | AGTATGTATC | AAATACACAT | 150 |
| ATGGAAAAAA | TTAACTATTC | ATAATTTAAA | AAATAGAAAA | GATACATCTA | 200 |
| GTGAAATTAG | GTGCATGTAT | CAAATACATT | AGGAAAAGGG | CATATATCTT | 250 |
| GATCTAGATA | ATTAACGATT | TTGATTTATG | TATAATTTCC | AAATGAAGGT | 300 |
| TTATATCTAC | TTCAGAAATA | ACAATATACT | TTTATCAGAA | CATTCAACAA | 350 |
| AGCAACAACC | AACTAGAGTG | AAAAATACAC | ATTGTTCTCT | AGACATACAA | 400 |
| AATTGAGAAA | AGAATCTCAA | AATTTAGAGA | AACAAATCTG | AATTTCTAGA | 450 |
| AGAAAAAAAT | AATTATGCAC | TTTGCTATTG | CTCGAAAAAT | AAATGAAAGA | 500 |
| AATTAGACTT | TTTTAAAAGA | TGTTAGACTA | GATATACTCA | AAAGCTATTA | 550 |
| AAGGAGTAAT | ATTCTTCTTA | CATTAAGTAT | TTTAGTTACA | GTCCTGTAAT | 600 |

TABLE 2-continued

NUCLEOTIDE SEQUENCE OF POTATO UBIQUITIN-RIBOSOMAL
FUSION PROMOTER (UBI3) AND UBIQUITIN CODING REGION
INSERT, AND UBIQUITIN-LYTIC PEPTIDE FUSION GENE CONSTRUCT

```
TAAAGACACA TTTTAGATTG TATCTAAACT TAAATGTATC TAGAATACAT    650

ATATTTGAAT GCATCATATA CATGTATCCG ACACACCAAT TCTCATAAAA    700

AACGTAATAT CCTAAACTAA TTTATCCTTC AAGTCAACTT AAGCCCAATA    750

TACATTTTCA TCTCTAAAGG CCCAAGTGGC ACAAAATGTC AGGCCCAATT    800

ACGAAGAAAA GGGCTTGTAA AACCCTAATA AAGTGGCACT GGCAGAGCTT    850

ACACTCTCAT TCCATCAACA AAGAAACCCT AAAAGCCGCA GCGCCACTGA    900

TTTCTCTCCT CCAGGCGAAG ATG CAG ATC TTC GTG AAG ACC TTA    944
                     Met Gln Ile Phe Val Lys Thr Leu
                       1               5

ACG GGG AAG ACG ATC ACC CTA GAG GTT GAG TCT TCC GAC ACC    986
Thr Gly Lys Thr Ile Thr Leu Glu Val Glu Ser Ser Asp Thr
        10              15                  20

ATC GAC AAT GTC AAA GCC AAG ATC CAG GAC AAG GAA GGG ATT   1028
Ile Asp Asn Val Lys Ala Lys Ile Gln Asp Lys Glu Gly Ile
            25              30                  35

CCC CCA GAC CAG CAG CGT TTG ATT TTC GCC GGA AAG CAG CTT   1070
Pro Pro Asp Gln Gln Arg Leu Ile Phe Ala Gly Lys Gln Leu
                40              45                  50

GAG GAT GGT CGT ACT CTT GCC GAC TAC AAC ATC°CAG AAG GAG   1112
Glu Asp Gly Arg Thr Leu Ala Asp Tyr Asn Ile Gln Lys Glu
                    55              60

TCA ACT CTC CAT CTC GTG CTC CGT CTC CGT GGT GGT           1148
Ser Thr Leu His Leu Val Leu Arg Leu Arg Gly Gly
65                  70                  75

GGA TCC GCT GTT AAA AGA GTG GGT CGT AGG TTG AAA AAG TTG   1190
Gly Ser Ala Val Lys Arg Val Gly Arg Arg Leu Lys Lys Leu
                80              85                  90

GAC CGT AAG ATT GAT AGG TTA GGA GTT GAT TTT TGATC         1228
Asp Arg Lys Ile Asp Arg Leu Gly Val Asp Phe
                95              100
```

SEQ ID NO. 93

```
CCAAAGCACA TACTTATCGA TTTAAATTTC ATCGAAGAGA TTAATATCGA     50

ATAATCATAT ACATACTTTA AATACATAAC AAATTTTAAA TACATATATC    100

TGGTATATAA TTAATTTTTT AAAGTCATGA AGTATGTATC AAATACACAT    150

ATGGAAAAAA TTAACTATTC ATAATTTAAA AAATAGAAAA GATACATCTA    200

GTGAAATTAG GTGCATGTAT CAAATACATT AGGAAAAGGG CATATATCTT    250

GATCTAGATA ATTAACGATT TGATTTATG TATAATTTCC AAATGAAGGT     300

TTATATCTAC TTCAGAAATA ACAATATACT TTTATCAGAA CATTCAACAA    350

AGCAACAACC AACTAGAGTG AAAAATACAC ATTGTTCTCT AGACATACAA    400

AATTGAGAAA AGAATCTCAA AATTTAGAGA AACAAATCTG AATTTCTAGA    450

AGAAAAAAAT AATTATGCAC TTTGCTATTG CTCGAAAAAT AAATGAAAGA    500

AATTAGACTT TTTTAAAAGA TGTTAGACTA GATATACTCA AAAGCTATTA    550

AAGGAGTAAT ATTCTTCTTA CATTAAGTAT TTTAGTTACA GTCCTGTAAT    600

TAAAGACACA TTTTAGATTG TATCTAAACT TAAATGTATC TAGAATACAT    650

ATATTTGAAT GCATCATATA CATGTATCCG ACACACCAAT TCTCATAAAA    700
```

TABLE 2-continued

NUCLEOTIDE SEQUENCE OF POTATO UBIQUITIN-RIBOSOMAL
FUSION PROMOTER (UBI3) AND UBIQUITIN CODING REGION
INSERT, AND UBIQUITIN-LYTIC PEPTIDE FUSION GENE CONSTRUCT

| | | | | | | | | | | |
|---|---|---|---|---|---|---|---|---|---|---|
| AACGTAATAT | CCTAAACTAA | TTTATCCTTC | AAGTCAACTT | AAGCCCAATA | | | | | | 750 |
| TACATTTTCA | TCTCTAAAGG | CCCAAGTGGC | ACAAAATGTC | AGGCCCAATT | | | | | | 800 |
| ACGAAGAAAA | GGGCTTGTAA | AACCCTAATA | AAGTGGCACT | GGCAGAGCTT | | | | | | 850 |
| ACACTCTCAT | TCCATCAACA | AAGAAACCCT | AAAAGCCGCA | GCGCCACTGA | | | | | | 900 |
| TTTCTCTCCT | CCAGGCGAAG | ATG | CAG | ATC | TTC | GTG | AAG | ACC | TTA | 944 |
| | | Met | Gln | Ile | Phe | Val | Lys | Thr | Leu | |
| | | 1 | | | | 5 | | | | |
| ACG | GGG | AAG | ACG | ATC | ACC | CTA | GAG | GTT | GAG | TCT | TCC | GAC | ACC | 986 |

| | | | | | | | | | | | | | | |
|---|---|---|---|---|---|---|---|---|---|---|---|---|---|---|
| ACG GGG AAG ACG ATC ACC CTA GAG GTT GAG TCT TCC GAC ACC | 986 |
| Thr Gly Lys Thr Ile Thr Leu Glu Val Glu Ser Ser Asp Thr | |
| 10    15    20 | |
| ATC GAC AAT GTC AAA GCC AAG ATC CAG GAC AAG GAA GGG ATT | 1028 |
| Ile Asp Asn Val Lys Ala Lys Ile Gln Asp Lys Glu Gly Ile | |
| 25    30    35 | |
| CCC CCA GAC CAG CAG CGT TTG ATT TTC GCC GGA AAG CAG CTT | 1070 |
| Pro Pro Asp Gln Gln Arg Leu Ile Phe Ala Gly Lys Gln Leu | |
| 40    45    50 | |
| GAG GAT GGT CGT ACT CTT GCC GAC TAC AAC ATC CAG AAG GAG | 1112 |
| Glu Asp Gly Arg Thr Leu Ala Asp Tyr Asn Ile Gln Lys Glu | |
| 40    45    50 | |
| TCA ACT CTC CAT CTC GTG CTC CGT CTC CGT GGT GGT GGA TCC | 1154 |
| Ser Thr Leu His Leu Val Leu Arg Leu Arg Gly Gly Gly Ser | |
| 65    70    75 | |

EXAMPLE 3

Construction of Ubiquitin-lytic Peptide Fusion Plasmids With Polyubiquitin Promoter and Intron (Ubi7)

Exemplary and preferred pUC19 and pCGN1547 plasmid vectors containing a potato (Solanum tuberosum) polyubiquitin promoter and intron (Ubi7), a region coding for a ubiquitin polypeptide, and a gene coding for a lytic peptide are constructed.

To obtain the genomic clone containing a polyubiquitin promoter, intron and ubiquitin polypeptide coding region, a λFIXII potato genomic library was first prescreened using PCR as described in Example 2 above. The PCR primers are homologous to regions of the polyubiquitin cDNA (see Garbarino J., et al., Plant Molecular Biology 20: 235(1992)). A primer homologous to the 5' untranslated region of ubiquitin in the polyubiquitin cDNA and a primer complementary to the amino terminus of the ubiquitin coding region in the polyubiquitin cDNA are used. A genomic clone containing both the polyubiquitin promoter region, intron, and the polyubiquitin coding region was identified.

A chimeric gene is then constructed with a portion of the potato polyubiquitin genomic clone ligated to a lytic peptide gene, as described in Example 2. PCR is used to generate the Ubi7-ubiquitin portion of the chimeric gene. The Ubi7 promoter region includes the 1220 bp promoter and 568 bp intron upstream of the ubiquitin ATG, and the ubiquitin polypeptide coding region is 328 bp plus 6 bp of a BamHI restriction site (SEQ ID NO. 96). This plasmid is designated pUCUbi7.

A nucleotide fragment coding for the lytic peptide corresponding to the amino acid sequence SEQ ID NO. 98) is generated as described in Example 2. The resulting Ubi7 ubiquitin-lytic peptide fusion gene construct corresponds to SEQ ID NO. 95. Unlike previous cloning attempts using the CaMV35S promoter as described in the Background section, the sequence does not reveal any point mutations in the lytic peptide sub-clones. The plasmid was stable in the E. coli host and did not inhibit its growth.

Figure 2:
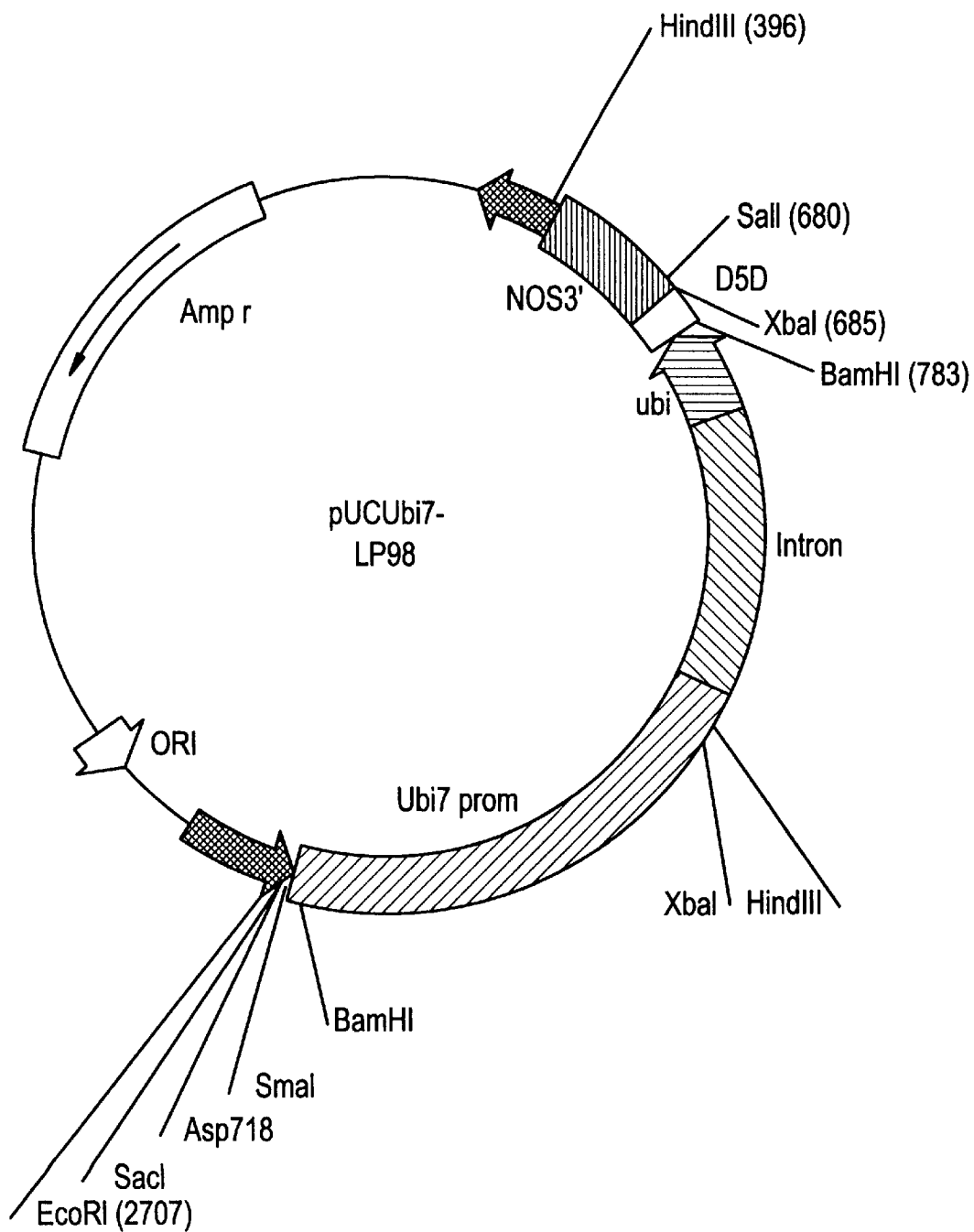
FIG. 2 is a map of a recombinant nucleic acid expression vector pUCUbi7-LP98 containing a 1220 bp polyubiquitin promoter region and 568 bp intron linked to a 228 bp coding region for a ubiquitin polypeptide with a six bp BamHI site at the 3' end (SEQ ID NO. 96) that is fused at its 3' end to a gene coding for a lytic peptide (D5D*, SEQ ID NO. 98). The Ubi7 ubiquitin-lytic peptide nucleotide sequence corresponds to SEQ ID NO. 95. A nopaline synthase polyadenylation signal is located at the 3' end of the lytic peptide gene.

The resulting pUC19 recombinant plasmid is shown in the plasmid map in FIG. 2. The sequence for the PCR insert containing the polyubiquitin promoter, intron, and the ubiquitin coding region corresponds to SEQ ID NO. 96 in Table 3 below. The sequence for the chimeric Ubi7 ubiquitin-lytic peptide fusion gene construct corresponds to SEQ ID NO. 95 in Table 3 below. This plasmid is designated as pUCUbi7-LP98.

The entire Ubi7 ubiquitin-lytic peptide fusion gene construct, including the polyadenylation site, is isolated from pUC19 as an Asp78/partial HindIII: restriction fragment (the intron has an internal HindIII site) and sub-cloned into the pCGN1547 Agrobacterium vector for use in plant transformation. This plasmid is designated pCGNUbi7-LP98.

TABLE 3

NUCLEOTIDE SEQUENCE OF POTATO POLYUBIQUITIN PROMOTER
REGION (UB17) AND UBIQUITIN CODING REGION INSERT,
AND UBIQUITIN-LYTIC PRPTIDE FUSION GENE CONSTRUCT

SEQ ID NO. 95

| | | | | |
|---|---|---|---|---|
| TTTATCAATC | AGATTTGAAC | ATATAAATAA | ATATAAATTG | TCTCAATAAT | 50 |
| TCTACATTAA | ACTAATATTT | GAAATCTCAA | TTTTATGATT | TTTTAAATTC | 100 |
| ACTTTATATC | CAAGACAATT | TNCANCTTCA | AAAAGTTTTA | TTAAANATTT | 150 |
| ACATTAGTTT | TGTTGATGAG | GATGACAAGA | TNTTGGTCAT | CAATTACATA | 200 |
| TACCCAAATT | GAATAGTAAG | CAACTTCAAT | CTTTTTCATA | ATGATAATGA | 250 |
| CAGACACAAN | NNAAACCCAT | TTATTATTCA | CATTGATTGA | GTTTTATATG | 300 |
| CAATATAGTA | ATAATAATAA | TATTTCTTAT | AAAGCAAGAG | GTCAATTTTT | 350 |
| TTTTAATTAT | ACCACGTCAC | TAAATTATAT | TTGATAATGT | AAAACAATTC | 400 |
| AAATTTTACT | TAAATATCAT | GAAATAAACT | ATTTTTATAA | CCAAATTACT | 450 |
| AAATTTTTCC | AATAAAAAAA | AGTCATTAAG | AAGACATAAA | ATAAATTTGA | 500 |
| GGTAAANGAG | TGAAGTCGAC | TGACTTTTTT | TTTTTTTATC | ATAAGAAAAT | 550 |
| AAATTATTAA | CTTTAACCTA | ATAAAACACT | AATATAATTT | CATGGAATCT | 600 |
| AATACTTACC | TCTTAGAAAT | AAGAAAAAGT | GTTTCTAATA | GACCCTCAAT | 650 |
| TTACATTAAA | TATTTTCAAT | CAAATTTAAA | TAACAAATAT | CAATATGAGG | 700 |
| TCAATAACAA | TATCAAAATA | ATATGAAAAA | AGAGCAATAC | ATAATATAAG | 750 |
| GGACGATTTA | AGTGCGATTA | TCAAGGTAGT | ATTATATCCT | AATTTGCTAA | 800 |
| TATTTGNGCT | CTTATATTTA | AGGTCATGTT | CATGATAAAC | TTGAAATGCG | 850 |
| CTATATTAGA | GCATATATTA | AAATAAAAAA | ATACCTAAAA | TAAAATTAAG | 900 |
| TTATTTTTAG | TATATATTTT | TTTACATGAC | CTACATTTTT | CTGGGTTTTT | 950 |
| CTAAAGGAGC | GTGTAAGTGT | CGACCTCATT | CTCCTAATTT | TCCCCACCAC | 1000 |
| ATAAAAATTA | AAAAGGAAAG | GTAGCTTTTG | CGTGTTGTTT | TGGTACACTA | 1050 |
| CACCTCATTA | TTACACGTGT | CCTCATATAA | TTGGTTAACC | CTATGAGGCG | 1100 |
| GTTTCGTCTA | GAGTCGGCCA | TGCCATCTAT | AAAATGAAGC | TTTCTGCACC | 1150 |
| TCATTTTTTT | CATCTTCTAT | CTGATTTCTA | TTATAATTTC | TCTCAATTGC | 1200 |
| CTTCAAATTT | CTCTTTAAGG | TTAGAATCTT | CTCTATTTTT | | 1240 |
| GGTTTTTGTA | TGTTTAGATT | CTCGAATTAG | CTAATCAGGC | GCTGTTATAG | 1290 |
| CCCTTCCTTT | TGAGTCTCTC | CTCGGTTGTC | TTGATGGAAA | AGGCCTAACA | 1340 |
| TTTGAGTTTT | TTTACGTCTG | GTTTGATGGA | AAAGGCCTAC | AATTGGCCGT | 1390 |
| TTTCCCCGTT | CGTTTTGATG | AAAAAGCCCC | TAGTTTGAGA | TTTTTTTTCT | 1440 |
| GTCGTTCGTT | CTAAAGGTTT | AAAATTAGAG | TTTTTACATT | TGTTTGATGA | 1490 |
| AAAAGGCCTT | AAATTTGAGT | TTTTCCGGTT | GATTTGATGA | AAAAGCCCTA | 1540 |
| GAATTTGTGT | TTTTCCGTCG | GTTTGATTCT | GAAGGCCTAA | AATTTGAGTT | 1590 |
| TCTCCGGCTG | TTTTGATGAA | AAAGCCCTAA | ATTTGAGTTT | CTCCGGCTGT | 1640 |
| TTTGATGAAA | AAGCCCTAAA | TTTGAAGTTT | TTTCCCCGTG | TTTTAGATTG | 1690 |
| TTTAGGTTTT | AATTCTCGAA | TCAGCTAATC | AGGGAGTGTG | AAAGCCCTAA | 1740 |
| ATTGAAGTTT | TTTTCGTTGT | TCTGATTGTT | GTTTTTATGA | ATTTGCAG | 1788 |
| ATG CAG ATC TTT GTG AAA ACT CTC ACC GGA AAG ACT ATC ACC | | | | | 1830 |

TABLE 3-continued

NUCLEOTIDE SEQUENCE OF POTATO POLYUBIQUITIN PROMOTER
REGION (UB17) AND UBIQUITIN CODING REGION INSERT,
AND UBIQUITIN-LYTIC PRPTIDE FUSION GENE CONSTRUCT

| Met Gln Ile Phe Val Lys Thr Leu Thr Gly Lys Thr Ile Thr | |
|---|---|
| 1           5                  10 | |
| CTA GAG GTG GAA AGT TCT GAT ACA ATC GAC AAC GTT AAG GCT | 1872 |
| Leu Glu Val Glu Ser Ser Asp Thr Ile Asp Asn Val Lys Ala | |
| 15              20                  25 | |
| AAG ATC CAG GAT AAG GAA GGA ATT CCC CCG GAT CAG CAA AGG | 1914 |
| Lys Ile Glu Asp Lys Glu Gly Ile Pro Pro Asp Gln Gln Arg | |
| 30              35                  40 | |
| CTT ATC TTC GCC GGA AAG CAG TTG GAG GAC GGA CGT ACT CTA | 1956 |
| Leu Ile Phe Ala Gly Lys Gln Leu Glu Asp Gly Arg Thr Leu | |
| 45              50                  55 | |
| GCT GAT TAC AAC ATC CAG AAG GAG TCT ACC CTC CAT TTG GTG | 1998 |
| Ala Asp Tyr Asn Ile Gln Lys Glu Ser Thr Leu His Leu Val | |
| 60              65                  70/ | |
| CTC CGT CTA CGT GGA GGT GGA TCC GCT GTT AAA AGA GTG GGT | 2040 |
| Leu Arg Leu Arg Gly Gly Gly Ser Ala Val Lys Arg Val Gly | |
| 75              80 | |
| CGT AGG TTG AAA AAG TTG GAC CGT AAG ATT GAT AGG TTA GGA | 2082 |
| Arg Arg Leu Lys Lys Leu Asp Arg Lys Ile Asp Arg Leu Gly | |
| 85              90                  95 | |
| GTT GAT TTT TGATCTAGAG CCCCGAATTT CCCCGA | 2127 |
| Val Asp Phe | |
| 100 | |

SEQ ID NO 96

| TTTATCAATC AGATTTGAAC ATATAAATAA ATATAAATTG TCTCAATAAT | 50 |
|---|---|
| TCTACATTAA ACTAATATTT GAAATCTCAA TTTTATGATT TTTTAAATTC | 100 |
| ACTTTATATC CAAGACAATT TNCANCTTCA AAAAGTTTTA TTAAANATTT | 150 |
| ACATTAGTTT TGTTGATGAG GATGACAAGA TNTTGGTCAT CAATTACATA | 200 |
| TACCCAAATT GAATAGTAAG CAACTTCAAT GTTTTCATA ATGATAATGA | 250 |
| CAGACACAAN NNAAACCCAT TTATTATTCA CATTGATTGA GTTTTATATG | 300 |
| CAATATAGTA ATAATAATAA TATTTCTTAT AAAGCAAGAG GTCAATTTTT | 350 |
| TTTTAATTAT ACCACGTCAC TAAATTATAT TTGATAATGT AAAACAATTC | 400 |
| AAATTTTACT TAAATATCAT GAAATAAACT ATTTTTATAA CCAAATTACT | 450 |
| AAATTTTTCC AATAAAAAAA AGTCATTAAG AAGACATAAA ATAAATTTGA | 500 |
| GGTAAANGAG TGAAGTCGAC TGACTTTTTT TTTTTTTATC ATAAGAAAAT | 550 |
| AAATTATTAA CTTTAACCTA ATAAAACACT AATATAATTT CATGGAATCT | 600 |
| AATACTTACC TCTTAGAAAT AAGAAAAAGT GTTTCTAATA GACCCTCAAT | 650 |
| TTACATTAAA TATTTTCAAT CAAATTTAAA TAACAAATAT CAATATGAGG | 700 |
| TCAATAACAA TATCAAAATA ATATGAAAAA AGAGCAATAC ATAATATAAG | 750 |
| GGACGATTTA AGTGCGATTA TCAAGGTAGT ATTATATCCT AATTTGCTAA | 800 |
| TATTTGNGCT CTTATATTTA AGGTCATGTT CATGATAAAC TTGAAATGCG | 850 |
| CTATATTAGA GCATATATTA AAATAAAAAA ATACCTAAAA TAAAATTAAG | 900 |
| TTATTTTTAG TATATATTTT TTTACATGAC CTACATTTTT CTGGGTTTTT | 950 |
| CTAAAGGAGC GTGTAAGTGT CGACCTCATT CTCCTAATTT TCCCCACCAC | 1000 |
| ATAAAAATTA AAAAGGAAAG GTAGCTTTTG CGTGTTGTTT TGGTACACTA | 1050 |

TABLE 3-continued

NUCLEOTIDE SEQUENCE OF POTATO POLYUBIQUITIN PROMOTER
REGION (UB17) AND UBIQUITIN CODING REGION INSERT,
AND UBIQUITIN-LYTIC PRPTIDE FUSION GENE CONSTRUCT

| | |
|---|---|
| CACCTCATTA TTACACGTGT CCTCATATAA TTGGTTAACC CTATGAGGCG | 1100 |
| GTTTCGTCTA GAGTCGGCCA TGCCATCTAT AAAATGAAGC TTTCTGCACC | 1150 |
| TCATTTTTTT CATCTTCTAT CTGATTTCTA TTATAATTTC TCTCAATTGC | 1200 |
| CTTCAAATTT CTCTTTAAGG TTAGAATCTT CTCTATTTTT | 1240 |
| GGTTTTTGTA TGTTTAGATT CTCGAATTAG CTAATCAGGC GCTGTTATAG | 1290 |
| CCCTTCCTTT TGAGTCTCTC CTCGGTTGTC TTGATGGAAA AGGCCTAACA | 1340 |
| TTTGAGTTTT TTTACGTCTG GTTTGATGGA AAAGGCCTAC AATTGGCCGT | 1390 |
| TTTCCCCGTT CGTTTTGATG AAAAAGCCCC TAGTTTGAGA TTTTTTTTCT | 1440 |
| GTCGTTCGTT CTAAAGGTTT AAAATTAGAG TTTTTACATT TGTTTGATGA | 1490 |
| AAAAGGCCTT AAATTTGAGT TTTTCCGGTT GATTTGATGA AAAAGCCCTA | 1540 |
| GAATTTGTGT TTTTCCGTCG GTTTGATTCT GAAGGCCTAA AATTTGAGTT | 1590 |
| TCTCCGGCTG TTTTGATGAA AAAGCCCTAA ATTTGAGTTT CTCCGGCTGT | 1640 |
| TTTGATGAAA AAGCCCTAAA TTTGAAGTTT TTTCCCCGTG TTTTAGATTG | 1690 |
| TTTAGGTTTT AATTCTCGAA TCAGCTAATC AGGGAGTGTG AAAGCCCTAA | 1740 |
| ATTGAAGTTT TTTTCGTTGT TCTGATTGTT GTTTTTATGA ATTTGCAG | 1788 |
| ATG CAG ATC TTT GTG AAA ACT CTC ACC GGA AAG ACT ATC ACC<br>Met Gln Ile Phe Val Lys Thr Leu Thr Gly Lys Thr Ile Thr<br>1               5               10 | 1830 |
| CTA GAG GTG GAA AGT TCT GAT ACA ATC GAC AAC GTT AAG GCT<br>Leu Glu Val Glu Ser Ser Asp Thr Ile Asp Asn Val Lys Ala<br>15              20              25 | 1872 |
| AAG ATC CAG GAT AAG GAA GGA ATT CCC CCG GAT CAG CAA AGG<br>Lys Ile Glu Asp Lys Glu Gly Ile Pro Pro Asp Gln Gln Arg<br>    30               35             40 | 1914 |
| CTT ATC TTC GCC GGA AAG CAG TTG GAG GAC GGA CGT ACT CTA<br>Leu Ile Phe Ala Gly Lys Gln Leu Glu Asp Gly Arg Thr Leu<br>      45               50             55 | 1956 |
| GCT GAT TAC AAC ATC CAG AAG GAG TCT ACC CTC CAT TTG GTG<br>Ala Asp Tyr Asn Ile Gln Lys Glu Ser Thr Leu His Leu Val<br>          60                 65             70 | 1998 |
| CTC CGT CTA CGT GGA GGT GGA TCC<br>Leu Arg Leu Arg Gly Gly Gly Ser<br>                  75 | 2022 |

EXAMPLE 4

Construction of Ubiquitin-Lytic Peptide Fusion Gene Plasmid Vectors pUC19 and pCGN1547 plasmid vectors containing a potato (*Solanum tuberosum*) Ubi3 promoter, a region coding for a ubiquitin polypeptide, and a gene coding for a lytic peptide are constructed according to Example 2. Each plasmid respectively contains one lytic peptide nucleotide sequence coding for an amino acid sequence corresponding to SEQ ID NO. 1, 7, 15, 21, 30, 39, 43, 52, 83, 86, 88, 90, and 91. The resultant pUC19 Ubi3 ubiquitin-lytic peptide recombinant plasmids are designated as follows: pUCUbi3-LP1, pUCUbi3-LP7, pUCUbi3-LP15, pUCUbi3-LP21, pUCUbi3-LP30, pUCUbi3-LP39, pUCUbi3-LP43, pUCUbi3-LP52, pUCUbi3-LP83, pUCUbi3-LP86, pUCUbi3-LP88, pUCUbi3-LP90, and pUCUbi3-LP91. The resultant pCGN1547 Ubi3 ubiquitin-lytic peptide recombinant plasmids are designated as follows: pCGNUbi3-LP1, pCGNUbi3-LP7, pCGNUbi3-LP15, pCGNUbi3-LP21, pCGNUbi3-LP30, pCGNUbi3-LP39, pCGNUbi3-LP43, pCGNUbi3-LP52, pCGNUbi3-LP83, pCGNUbi3-LP86, pCGNUbi3-LP88, pCGNUbi3-LP90, and pCGNUbi3-LP91.

pUC19 and pCGN1547 plasmid vectors containing a potato (*Solanum tuberosum*) Ubi7 promoter and intron, a region coding for a ubiquitin polypeptide, and a gene coding for a lytic peptide are constructed according to Example 3. Each plasmid respectively contains one lytic peptide nucleotide sequence coding for an amino acid sequence corresponding to SEQ ID NO. 1, 7, 15, 21, 30, 39, 43, 52, 83, 86, 88, 90, and 91. The resultant pUC19 Ubi7 ubiquitin-lytic peptide recombinant plasmids are designated as follows: pUCUbi7-LP1, pUCUbi7-LP7, pUCUbi7-LP15, pUCUbi7-LP21, pUCUbi7-LP30, pUCUbi7-P39, pUCUbi7-LP43, pUCUbi7-LP52, pUCUbi7-LP83, pUCUbi7-LP86, pUCUbi7-LP88, pUCUbi7-LP90, and pUCUbi7-LP91. The resultant pCGN1547 Ubi7 ubiquitin-lytic peptide recombinant plasmids are designated as follows: pCGNUbi7-LP1, pCGNUbi7-LP7, pCGNUbi7-LP15, pCGNUbi7,-LP21, pCGNUbi7-LP30, pCGNUbi7-LP39, pCGNUbi7-LP43, pCGNUbi7-LP52, pCGNUbi7-LP83, pCGNUbi7-LP86, pCGNUbi7-LP88, pCGNUbi7-LP90, and pCGNUbi7-LP91.

EXAMPLE 5

Construction of GUS-Ubiquitin Fusion Gene Recombinant DNA Molecules and Ubiquitin Promoter-GUS Recombinant DNA Molecules Two chimeric genes containing a β-glucuronidase (GUS) reporter gene and the Ubi3 promoter were constructed in-pCGN1547 plasmid vectors according to Garbarino, J., and Belknap, W., Plant Molecular Biology 24: 119 (1994), hereby incorporated by reference in its entirety. The first vector contains the 920 bp Ubi3 promoter ligated to the GUS gene, and expresses the GUS protein. This plasmid is designated pCGNUbi3-GUS. The second vector contains the 920 bp Ubi3 promoter and 228 bp ubiquitin coding region ligated in frame to the GUS gene. This plasmid expresses a ubiquitin-GUS fusion polypeptide. This plasmid is designated pCGNUbi3-GUSf.

Two chimeric genes containing a β-glucuronidase (GUS) reporter gene and the Ubi7 promoter minus the intron region were constructed in pCGN1547 plasmid vectors using PCR, as described in Example 3 and in Garbarino, J., and Belknap, W., Plant Molecular Biology 24: 119 (1994). The first vector contains a 1156 bp Ubi7 promoter region insert, including she 5' untranslated region of ubiquitin, ligated to the GUS gene. This plasmid does not contain the Ubi7 intron and expresses the GUS protein. This plasmid is designated pCGNUbi7-GUS. The second vector contains the 1156 Ubi7 ubiquitin promoter from pCGNUbi7-GUS and the 228 bp ubiquitin coding region fused in frame to the GUS reporter gene. This plasmid expresses a ubiquitin-GUS fusion polypeptide and is designated pCGNUbi7-GUSf.

EXAMPLE 6

Plant Transformation and GUS Gene Expression

The chimeric plasmids pCGNUbi3-GUS, pCGNUbi3-GUSf, pCGNUbi7-GUS, and pCGNUbi7-GUSf from Example 5 are introduced into the potato (*Solanum tuberosum*) using Agrobacterium mediated transformation according to Garbarino, J., and Belknap, W. Plant Molecular Biology 24:119 (1994). The strain of *Agrobacterium tumefaciens* used for transformation (PC2760, see An, G., et al., EMBO J. 4: 277 (1985)) harbors the disarmed Ti plasmid pAL4404 (see Hoekema, A., et al., Nature 303: 179 (1983). Plant transformation is carried out as previously described in Synder, G. W., et al., Plant Cell Rep 12:324 (1993), except that 1 mg/l silver thiosulfate is added to the stage II transformation medium (see Chang, H. H., et al., Bot Bull Acad Sci 32: 63 (1991).

Expression of the ubiquitin-GUS fusion polypeptide and MRNA products and the GUS protein alone is examined by northern and western analysis, as described in Garbarino J., and Belknap, W., Plant Molecular Biology 24: 119 (1994). GUS protein expression is examined in the transgenic plants using western analysis. Although there is a wide range of activity among individual clones, the ubiquitin-GUS fusion polypeptide containing plants generally give 5–10 fold higher expression than the plants containing GUS protein alone. This higher level of protein expression Corresponds to similarly elevated mRNA transcription levels for the ubiquitin-GUS fusion constructs, as shown by northern analysis (described in Garbarino et al., Plant Molecular Biology 24: 119 (1994)). Western analysis also shows that the ubiquitin-GUS fusion polypeptide was appropriately processed by endogenous ubiquitin hydrolases co produce free GUS protein.

GUS protein activity is measured as described by Jefferson, R. A., et al., EMBO J. 6: 3901 (1987). Table 4 below shows a comparison of the GUS activities in plants transformed with pCGNUbi3-GUS (ubi-) and plants transformed with pCGNUbi3-GUSf (ubi+). The activity is measured in nmoles methyl umbelliferon (MU) per minute per milligram of protein. Methyl umbelliferon is the fluorescent product of the GUS enzymatic reaction.

TABLE 4

COMPARISON OF GUS PROTEIN ACTIVITY IN PLANTS TRANSFORMED WITH THE UBI3 PROMOTER WITH (+UBI) AND WITHOUT (-UBI) UBIQUITIN POLYPEPTIDE FUSION

| | GUS Activity (nmoles MU/min/mg protein) | | | | |
|---|---|---|---|---|---|
| Construct | Leaf Meristem | 2nd Leaf | 5th Leaf | Senescent Leaf | Tuber |
| 3.2 – ubi | 6.31 ± 0.74 | 2.51 ± 0.52 | 1.79 ± 0.22 | 5.42 ± 1.24 | 3.26 ± 0.27 |
| 8.1 – ubi | 25.8 ± 2.08 | 9.98 ± 2.10 | 6.34 ± 1.00 | 19.20 ± 6.11 | 14.2 ± 1.6 |
| 3.5 + ubi | 94.8 ± 12.6 | 60.3 ± 25.1 | 32.7 ± 8.71 | 50.1 ± 11.6 | 37.6 ± 10.4 |
| 9.8 + ubi | 33.3 ± 0.5 | 18.9 ± 2.75 | 9.74 ± 0.99 | 22.7 ± 3.57 | 20.7 ± 3.45 |

EXAMPLE 7

Plant Transformation and Ubiquitin-Lytic Peptide Gene Expression

The chimeric plasmids pCGNUbi3-LP98 from Example 2 and pCGNUbi7-LP98 from Example 3 are introduced into the potato (*Solanum tuberosum*) using Agrobacterium mediated transformation according to Garbarino, J., and Belknap, W. Plant Molecular Biology 24:119 (1994). The strain of *Agrobacterium tumefaciens* used for transformation (PC2760, see An, G., et al., 3EMBO J. 4: 277 (1985)) harbors the disarmed Ti plasmid pAL4404 (see Hoekema, A., et al., Nature 303: 179 (1983). Plant transformation is carried out as previously described in Synder, G. W., et al., Plant Cell Rep 12:324 (1993), except that 1 mg/l silver thiosulfate is added to the stage II transformation medium (see Chang, H. H., et al., Bot Bull Acad Sci 32: 63 (1991).

Expression of the ubiquitin-lytic peptide fusion polypeptide and mRNA products is examined by northern and western analysis, in Garbarino J., and Belknap, W., Plant Molecular Biology 24: 119 (1994). Northern analysis shows that ubiquitin-lytic peptide mRNA is transcribed from the gene construct in the transgenic plants. Western analysis shows that the ubiquitin-lytic peptide fusion polypeptide is appropriately processed by endogenous ubiquitin in hydrolases to produce free lytic peptide.

EXAMPLE 8

Cloned Ubi3/Ubi7 Promoter Activity mRNA expression from the cloned Ubi3 promoter was examined before and after wounding to determine if the cloned Ubi3 promoter is wound inducible in transformed plants (see Garbarino, J. and Belknap, W., Plant Molecular Biology 24:119 (1994)). Northern analysis comparing endogenous Ubi3 mRNA expression levels to pCGNUbi3-GUS and pCGNUbi3-GUSf mRNA expression levels in transformed plants (see Example 5) shows that while the endogenous Ubi3 mRNA transcription increases upon wounding, transcription from the recombinant Ubi3 plasmids does not. Thus the recombinant Ubi3 promoter does not have the wound inducible characteristic of the endogenous Ubi3 promoter. This result suggests that the 920 bp of upstream sequence cloned in the Ubi3 genomic clone is not sufficient to obtain wound-dependent activation of the promoter. The promoter instead is constitutive, however, it still demonstrates developmental regulation, as shown in Table 4 above.

In contrast, the cloned TUi-b promoter retains its wound-dependent induction. Northern analysis comparing the endogenous Ubi7 mRNA expression levels to the expression levels from pCGNUbi7-GUS and pCGNUbi7-GUSf in transformed plants (see Example 5) shows that both the endogenous and the cloned Ubi7 promoter have wound-dependent activation.

DEPOSIT INFORMATION

*E. coli* cultures, each respectively transformed with pUCUbi7-LP98 (Local Accession No. PBT-0273), pUCUbi3-LP98 (Local Accession No. PBT-0276), pUCUbi7 (Local Accession No. PBT-0277), and pUCUbi3 (Local Accession No. PBT-0234) were deposited in the Agricultural Research Service Culture Collection (NRRL). The depository is located at located at 1815 North University Street, Peoria, Ill.,

---

What is claimed is:

1. A lytic peptide comprising the amino acid sequence of SEQ ID NO. 97.

2. A lytic peptide comprising an amino acid sequence selected from the group consisting of SEQ ID NOS. 48, 55–65.

3. A lytic peptide comprising an amino acid sequence selected from the group consisting of SEQ ID NOS. 66–80.

4. A lytic peptide of claim 2 wherein the peptide has the amino acid sequence of SEQ ID NO. 57.

5. A lytic peptide of claim 3 wherein the peptide has the amino acid sequence of SEQ ID NO. 66.

6. A lytic peptide of claim 2 wherein the peptide has the amino acid sequence of SEQ ID NO. 48.

* * * * *

UNITED STATES PATENT AND TRADEMARK OFFICE
CERTIFICATE OF CORRECTION

PATENT NO. : 5,955,573
DATED : SEPTEMBER 21, 1999
INVENTOR(S) : JESSE M. JAYNES

It is certified that error appears in the above-identified patent and that said Letters Patent is hereby corrected as shown below:

Title page, item [75],

Please delete inventors "Joan Garbarino" and "William Belknap."

Signed and Sealed this

Twenty-fourth Day of October, 2000

Attest:

Q. TODD DICKINSON

*Attesting Officer*     *Director of Patents and Trademarks*

SEQUENCE LISTING (1) GENERAL INFORMATION:

(iii) NUMBER OF SEQUENCES: 98

(2) INFORMATION FOR SEQ ID NO: 1:

(i) SEQUENCE CHARACTERISTICS:
      (A) LENGTH: 27
      (B) TYPE: AMINO ACID
      (C) TOPOLOGY: LINEAR (ii) MOLECULE TYPE:
      (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 1:

Phe Ala Val Ala Val Lys Ala Val Lys Lys Ala Val Lys Lys Val Lys
1            5                    10                 15

Lys Ala Val Lys Lys Ala Val Lys Lys Lys Lys
        20              25

(2) INFORMATION FOR SEQ ID NO: 2:

(i) SEQUENCE CHARACTERISTICS:
      (A) LENGTH: 32
      (B) TYPE: AMINO ACID
      (C) TOPOLOGY: LINEAR (ii) MOLECULE TYPE:
      (A) DESCRIPTION: PEPTIDE

-continued (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 2:

Phe Ala Val Ala Val Lys Ala Val Ala Val Lys Ala Val Lys Lys Ala
 1               5                  10                  15
Val Lys Lys Val Lys Lys Ala Val Lys Lys Ala Val Lys Lys Lys
                20                  25                  30

(2) INFORMATION FOR SEQ ID NO: 3:

(i) SEQUENCE CHARACTERISTICS:
             (A) LENGTH: 37
             (B) TYPE: AMINO ACID
             (C) TOPOLOGY: LINEAR (ii) MOLECULE TYPE:
             (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 3:

Phe Ala Val Ala Val Lys Ala Val Ala Val Lys Ala Val Ala Val Lys
 1               5                  10                  15
Ala Val Lys Lys Ala Val Lys Lys Val Lys Lys Ala Val Lys Lys Ala
                20                  25                  30
Val Lys Lys Lys Lys
                35

(2) INFORMATION FOR SEQ ID NO: 4:

(i) SEQUENCE CHARACTERISTICS:
             (A) LENGTH: 23
             (B) TYPE: AMINO ACID
             (C) TOPOLOGY: LINEAR (ii) MOLECULE TYPE:
             (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 4:

Phe Ala Val Ala Val Lys Ala Val Lys Lys Ala Val Lys Lys Val Lys
 1               5                  10                  15
Lys Ala Val Lys Lys Ala Val
                20

(2) INFORMATION FOR SEQ ID NO: 5:

(i) SEQUENCE CHARACTERISTICS:
        (A) LENGTH: 28
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 5:

```
Phe Ala Val Ala Val Lys Ala Val Ala Val Lys Ala Val Lys Lys Ala
1               5                  10                  15
Val Lys Lys Val Lys Lys Ala Val Lys Lys Ala Val
            20                  25
```

(2) INFORMATION FOR SEQ ID NO: 6:

(i) SEQUENCE CHARACTERISTICS:
        (A) LENGTH: 33
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 6:

```
Phe Ala Val Ala Val Lys Ala Val Ala Val Lys Ala Val Ala Val Lys
1               5                  10                  15
Ala Val Lys Lys Ala Val Lys Lys Val Lys Lys Ala Val Lys Lys Ala
            20                  25                  30
Val
```

(2) INFORMATION FOR SEQ ID NO: 7:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 7:

Phe Ala Val Gly Leu Arg Ala Ile Lys Arg Ala Leu Lys Lys Leu Arg
1               5                   10                  15

Arg Gly Val Arg Lys Val Ala Lys Arg Lys Arg
            20                  25

(2) INFORMATION FOR SEQ ID NO: 8:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 8:

Phe Ala Val Gly Leu Arg Ala Ile Lys Arg Ala Leu Lys Lys Leu Arg
1               5                   10                  15

Arg Gly Val Arg Lys Val Ala
            20

(2) INFORMATION FOR SEQ ID NO: 9:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 9:

Lys Arg Lys Arg Ala Val Lys Arg Val Gly Arg Arg Leu Lys Lys Leu
1               5                   10                  15

Ala Arg Lys Ile Ala Arg Leu Gly Val Ala Phe
            20                  25

(2) INFORMATION FOR SEQ ID NO: 10:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 10:

Ala Val Lys Arg Val Gly Arg Arg Leu Lys Lys Leu Ala Arg Lys Ile
 1               5                  10                  15

Ala Arg Leu Gly Val Ala Phe
             20

(2) INFORMATION FOR SEQ ID NO: 11:

(i) SEQUENCE CHARACTERISTICS:
          (A) LENGTH: 31
          (B) TYPE: AMINO ACID
          (C) TOPOLOGY: LINEAR (ii) MOLECULE TYPE:
          (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 11:

Phe Ala Val Gly Leu Arg Ala Ile Lys Arg Ala Leu Lys Lys Leu Arg
 1               5                  10                  15

Arg Gly Val Arg Lys Val Ala Lys Arg Lys Arg Lys Lys Asp Leu
             20                  25                  30

(2) INFORMATION FOR SEQ ID NO: 12:

(i) SEQUENCE CHARACTERISTICS:
          (A) LENGTH: 26
          (B) TYPE: AMINO ACID
          (C) TOPOLOGY: LINEAR (ii) MOLECULE TYPE:
          (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 12:

Phe Ala Val Gly Leu Arg Ala Ile Lys Arg Ala Leu Lys Lys Leu Arg
 1               5                  10                  15

Arg Gly Val Arg Lys Val Ala Lys Asp Leu
             20                  25

(2) INFORMATION FOR SEQ ID NO: 13:

(i) SEQUENCE CHARACTERISTICS:
          (A) LENGTH: 30
          (B) TYPE: AMINO ACID (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 13:

Lys Arg Lys Arg Ala Val Lys Arg Val Gly Arg Arg Leu Lys Lys Leu
1               5                   10                  15

Ala Arg Lys Ile Ala Arg Leu Gly Val Ala Phe Lys Asp Leu
            20                  25                  30

(2) INFORMATION FOR SEQ ID NO: 14:

(i) SEQUENCE CHARACTERISTICS:
        (A) LENGTH: 26
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 14:

Ala Val Lys Arg Val Gly Arg Arg Leu Lys Lys Leu Ala Arg Lys Ile
1               5                   10                  15

Ala Arg Leu Gly Val Ala Phe Lys Asp Leu
            20                  25

(2) INFORMATION FOR SEQ ID NO: 15:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 15:

Lys Lys Lys Lys Phe Val Lys Lys Val Ala Lys Lys Val Lys Lys Val
1               5                   10                  15

Ala Lys Lys Val Ala Lys Val Ala Val Ala Val
            20                  25

(2) INFORMATION FOR SEQ ID NO: 16:

(i) SEQUENCE CHARACTERISTICS:
        (A) LENGTH: 32
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 16:

```
Lys Lys Lys Lys Phe Val Lys Lys Val Ala Lys Lys Val Lys Lys Val
 1               5                  10                  15
Ala Lys Lys Val Ala Lys Val Ala Val Ala Lys Val Ala Val Ala Val
                20                  25                  30
```

(2) INFORMATION FOR SEQ ID NO: 17:

(i) SEQUENCE CHARACTERISTICS:
        (A) LENGTH: 37
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 17:

```
Lys Lys Lys Lys Phe Val Lys Val Ala Lys Lys Val Lys Lys Val
 1               5                  10                  15
Ala Lys Lys Val Ala Lys Val Ala Val Ala Lys Val Ala Val Ala Lys
                20                  25                  30
Val Ala Val Ala Val
            35
```

(2) INFORMATION FOR SEQ ID NO: 18:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 18:

```
Phe Val Lys Lys Val Ala Lys Lys Val Lys Lys Val Ala Lys Lys Val
 1               5                  10                  15
Ala Lys Val Ala Val Ala Val
            20
```

(2) INFORMATION FOR SEQ ID NO: 19:

(i) SEQUENCE CHARACTERISTICS:
      (A) LENGTH: 28
      (B) TYPE: AMINO ACID
      (C) TOPOLOGY: LINEAR (ii) MOLECULE TYPE:
      (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 19:

```
Phe Val Lys Lys Val Ala Lys Lys Val Lys Lys Val Ala Lys Lys Val
 1               5                  10                  15
Ala Lys Val Ala Val Ala Lys Val Ala Val Ala Val
            20                  25
```

(2) INFORMATION FOR SEQ ID NO: 20:

(i) SEQUENCE CHARACTERISTICS:
      (A) LENGTH: 33
      (B) TYPE: AMINO ACID
      (C) TOPOLOGY: LINEAR (ii) MOLECULE TYPE:
      (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 20:

```
Phe Val Lys Lys Val Ala Lys Lys Val Lys Lys Val Ala Lys Lys Val
 1               5                  10                  15
Ala Lys Val Ala Val Ala Lys Val Ala Val Ala Lys Val Ala Val Ala
            20                  25                  30
Val
```

(2) INFORMATION FOR SEQ ID NO: 21:

(i) SEQUENCE CHARACTERISTICS:
      (A) LENGTH: 27
      (B) TYPE: AMINO ACID
      (C) TOPOLOGY: LINEAR (ii) MOLECULE TYPE:

(A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 21:

Lys Lys Lys Lys Phe Val Lys Lys Val Ala Val Ala Lys Lys Val
 1               5                  10                  15

Ala Lys Val Ala Lys Lys Val Ala Lys Lys Val
            20                  25

(2) INFORMATION FOR SEQ ID NO: 22:

(i) SEQUENCE CHARACTERISTICS:
          (A) LENGTH: 32
          (B) TYPE: AMINO ACID
          (C) TOPOLOGY: LINEAR (ii) MOLECULE TYPE:
          (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 22:

Lys Lys Lys Lys Phe Val Lys Lys Val Ala Val Ala Lys Lys Val
 1               5                  10                  15

Ala Lys Val Ala Lys Lys Val Ala Lys Lys Val Ala Lys Lys Val Ala
            20                  25                  30

(2) INFORMATION FOR SEQ ID NO: 23:

(i) SEQUENCE CHARACTERISTICS:
          (A) LENGTH: 37
          (B) TYPE: AMINO ACID
          (C) TOPOLOGY: LINEAR (ii) MOLECULE TYPE:
          (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 23:

Lys Lys Lys Lys Phe Val Lys Lys Val Ala Val Ala Lys Lys Val
 1               5                  10                  15

Ala Lys Val Ala Lys Lys Val Ala Lys Lys Val Ala Lys Lys Val Ala
            20                  25                  30

Lys Val Ala Lys Lys
        35

(2) INFORMATION FOR SEQ ID NO: 24:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 24:

```
Phe Val Lys Lys Val Ala Lys Val Ala Lys Lys Val Ala Lys Val Ala
 1               5                  10                  15
Lys Lys Val Ala Lys Lys Val
            20
```

(2) INFORMATION FOR SEQ ID NO: 25:

(i) SEQUENCE CHARACTERISTICS:
        (A) LENGTH: 28
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 25:

```
Phe Val Lys Lys Val Ala Lys Val Ala Lys Lys Val Ala Lys Val Ala
 1               5                  10                  15
Lys Lys Val Ala Lys Lys Val Ala Lys Lys Val Ala
            20                  25
```

(2) INFORMATION FOR SEQ ID NO: 26:

(i) SEQUENCE CHARACTERISTICS:
        (A) LENGTH: 33
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED

```
    (xi) SEQUENCE DESCRIPTION: SEQ ID NO: 26:

Phe Val Lys Lys Val Ala Lys Val Ala Lys Val Ala Lys Val Ala
1               5                   10                  15

Lys Lys Val Ala Lys Lys Val Ala Lys Lys Val Ala Lys Val Ala Lys
            20                  25                  30

Lys (2) INFORMATION FOR SEQ ID NO: 27:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 27:

Phe Val Lys Lys Val Ala Lys Val Ala Lys Lys Val Ala Lys Val Ala
1               5                   10                  15

Lys Lys Val Ala Lys Lys Val Lys Lys Lys
            20                  25

(2) INFORMATION FOR SEQ ID NO: 28:

(i) SEQUENCE CHARACTERISTICS:
        (A) LENGTH: 32
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 28:

Phe Val Lys Lys Val Ala Lys Val Ala Lys Lys Val Ala Lys Val Ala
1               5                   10                  15

Lys Lys Val Ala Lys Lys Val Ala Lys Val Ala Lys Lys Lys
            20                  25                  30

(2) INFORMATION FOR SEQ ID NO: 29:

(i) SEQUENCE CHARACTERISTICS:
        (A) LENGTH: 37
        (B) TYPE: AMINO ACID
        (C) TOPOLOGY: LINEAR (ii) MOLECULE TYPE:
        (A) DESCRIPTION: PEPTIDE (iii) HYPOTHETICAL: NO
```

(v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 29:

Phe Val Lys Lys Val Ala Lys Val Ala Lys Val Ala Lys Val Ala
 1               5                  10                  15

Lys Lys Val Ala Lys Val Ala Lys Lys Val Ala Lys Val Ala Lys
            20                  25                  30

Lys Lys Lys Lys Lys
        35

(2) INFORMATION FOR SEQ ID NO: 30:

(i) SEQUENCE CHARACTERISTICS:
            (A) LENGTH: 16
            (B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 30:

Phe Lys Val Lys Ala Lys Val Lys Ala Lys Val Lys Lys Lys Lys Lys
 1               5                  10                  15

(2) INFORMATION FOR SEQ ID NO: 31:

(i) SEQUENCE CHARACTERISTICS:
            (A) LENGTH: 21
            (B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 31:

Phe Lys Val Lys Ala Lys Val Lys Ala Lys Val Lys Ala Lys Val Lys
 1               5                  10                  15

Ala Lys Lys Lys Lys
            20

(2) INFORMATION FOR SEQ ID NO: 32:

(i) SEQUENCE CHARACTERISTICS:
            (A) LENGTH: 27

(B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 32:

Phe Lys Val Lys Ala Lys Val Lys Ala Lys Val Lys Ala Lys Val Lys
 1               5                  10                  15

Ala Lys Val Lys Ala Lys Val Lys Lys Lys Lys
             20                  25

(2) INFORMATION FOR SEQ ID NO: 33:

(i) SEQUENCE CHARACTERISTICS:
            (A) LENGTH: 12
            (B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 33:

Phe Lys Val Lys Ala Lys Val Lys Ala Lys Val Lys
 1               5                  10

(2) INFORMATION FOR SEQ ID NO: 34:

(i) SEQUENCE CHARACTERISTICS:
            (A) LENGTH: 17
            (B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 34:

Phe Lys Val Lys Ala Lys Val Lys Ala Lys Val Lys Ala Lys Val Lys
 1               5                  10                  15

Ala (2) INFORMATION FOR SEQ ID NO: 35:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 35:

Phe Lys Val Lys Ala Lys Val Lys Ala Lys Val Lys Ala Lys Val Lys
1               5                  10                  15

Ala Lys Val Lys Ala Lys Val
            20

(2) INFORMATION FOR SEQ ID NO: 36:

(i) SEQUENCE CHARACTERISTICS:
        (A) LENGTH: 16
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 36:

Lys Lys Lys Lys Phe Lys Val Lys Ala Lys Val Lys Ala Lys Val Lys
1               5                  10                  15

(2) INFORMATION FOR SEQ ID NO: 37:

(i) SEQUENCE CHARACTERISTICS:
        (A) LENGTH: 21
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 37:

Lys Lys Lys Lys Phe Lys Val Lys Ala Lys Val Lys Ala Lys Val Lys
1               5                  10                  15

Ala Lys Val Lys Ala

20

(2) INFORMATION FOR SEQ ID NO: 38:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 38:

```
Lys Lys Lys Lys Phe Lys Val Lys Ala Lys Val Lys Ala Lys Val
 1               5                  10                  15
Ala Lys Val Lys Ala Lys Val Lys Ala Lys Val
            20                  25
```

(2) INFORMATION FOR SEQ ID NO: 39:

(i) SEQUENCE CHARACTERISTICS:
        (A) LENGTH: 25
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 39:

```
Phe Lys Lys Val Lys Lys Val Ala Lys Lys Val Cys Lys Cys Val Lys
 1               5                  10                  15
Lys Ala Val Lys Lys Val Lys Lys Phe
            20                  25
```

(2) INFORMATION FOR SEQ ID NO: 40:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 40:

Phe Ala Val Ala Val Lys Ala Val Lys Lys Ala Val Lys Val Lys
1               5                   10                  15

Lys Ala Val Lys Lys Ala Val Cys Cys Cys Cys
            20                  25

(2) INFORMATION FOR SEQ ID NO: 41:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 41:

Cys Cys Cys Cys Phe Val Lys Val Ala Lys Val Lys Lys Val
1               5                   10                  15

Ala Lys Lys Val Ala Lys Val Ala Val Ala Val
            20                  25

(2) INFORMATION FOR SEQ ID NO: 42:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 42:

Phe Ala Val Ala Val Lys Ala Val Lys Lys Ala Val Lys Val Lys
1               5                   10                  15

Lys Ala Val Lys Lys Ala Val Ser Ser Ser Ser
            20                  25

(2) INFORMATION FOR SEQ ID NO: 43:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 43:

Ser Ser Ser Ser Phe Val Lys Lys Val Ala Lys Lys Val Lys Lys Val
1               5                  10                  15

Ala Lys Lys Val Ala Lys Val Ala Val Ala Val
            20                  25

(2) INFORMATION FOR SEQ ID NO: 44:

(i) SEQUENCE CHARACTERISTICS:
            (A) LENGTH: 23
            (B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 44:

Phe Ala Leu Ala Leu Lys Ala Leu Lys Lys Ala Leu Lys Lys Leu Lys
1               5                  10                  15

Lys Ala Leu Lys Lys Ala Leu
            20

(2) INFORMATION FOR SEQ ID NO: 45:

(i) SEQUENCE CHARACTERISTICS:
            (A) LENGTH: 23
            (B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 45:

Leu Ala Lys Lys Leu Ala Lys Lys Leu Lys Lys Leu Ala Lys Lys Leu
1               5                  10                  15

Ala Lys Leu Ala Leu Ala Phe
            20

(2) INFORMATION FOR SEQ ID NO: 46:

(i) SEQUENCE CHARACTERISTICS:
            (A) LENGTH: 23
            (B) TYPE: AMINO ACID (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 46:

```
Phe Ala Phe Ala Phe Lys Ala Phe Lys Lys Ala Phe Lys Lys Phe Lys
 1               5                  10                  15

Lys Ala Phe Lys Lys Ala Phe
            20
```

(2) INFORMATION FOR SEQ ID NO: 47:

(i) SEQUENCE CHARACTERISTICS:
            (A) LENGTH: 23
            (B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 47:

```
Phe Ala Ile Ala Ile Lys Ala Ile Lys Lys Ala Ile Lys Lys Ile Lys
 1               5                  10                  15

Lys Ala Ile Lys Lys Ala Ile
            20
```

(2) INFORMATION FOR SEQ ID NO: 48:

(i) SEQUENCE CHARACTERISTICS:
            (A) LENGTH: 23
            (B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 48:

```
Phe Ala Lys Lys Phe Ala Lys Lys Phe Lys Lys Phe Ala Lys Lys Phe
 1               5                  10                  15

Ala Lys Phe Ala Phe Ala Phe
            20
```

(2) INFORMATION FOR SEQ ID NO: 49:

(i) SEQUENCE CHARACTERISTICS:
        (A) LENGTH: 17
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 49:

```
Phe Lys Arg Leu Ala Lys Ile Lys Val Leu Arg Leu Ala Lys Ile Lys
 1               5                  10                  15
Arg
```

(2) INFORMATION FOR SEQ ID NO: 50:

(i) SEQUENCE CHARACTERISTICS:
        (A) LENGTH: 37
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 50:

```
Lys Leu Lys Leu Ala Val Lys Leu Val Gly Leu Leu Arg Lys Lys Arg
 1               5                  10                  15
Ala Leu Lys Ile Ala Leu Arg Gly Val Ala Lys Arg Ala Gly Arg Leu
                20                  25                  30
Ala Val Arg Lys Phe
            35
```

(2) INFORMATION FOR SEQ ID NO: 51:

(i) SEQUENCE CHARACTERISTICS:
        (A) LENGTH: 26
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 51:

Phe Ala Arg Ala Arg Lys Ala Arg Lys Lys Ala Arg Lys Lys Arg Lys
1               5                   10                  15

Lys Ala Arg Lys Lys Ala Arg Lys Asp Arg
            20                  25

(2) INFORMATION FOR SEQ ID NO: 52:

(i) SEQUENCE CHARACTERISTICS:
         (A) LENGTH: 23
         (B) TYPE: AMINO ACID
         (C) TOPOLOGY: LINEAR (ii) MOLECULE TYPE:
         (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 52:

Phe Ala Val Ala Val Cys Ala Val Cys Cys Ala Val Cys Cys Val Cys
1               5                   10                  15

Cys Ala Val Cys Cys Ala Val
            20

(2) INFORMATION FOR SEQ ID NO: 53:

(i) SEQUENCE CHARACTERISTICS:
         (A) LENGTH: 23
         (B) TYPE: AMINO ACID
         (C) TOPOLOGY: LINEAR (ii) MOLECULE TYPE:
         (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 53:

Phe Ala Val Ala Val Ser Ala Val Ser Ser Ala Val Ser Ser Val Ser
1               5                   10                  15

Ser Ala Val Ser Ser Ala Val
            20

(2) INFORMATION FOR SEQ ID NO: 54:

(i) SEQUENCE CHARACTERISTICS:
         (A) LENGTH: 27
         (B) TYPE: AMINO ACID
         (C) TOPOLOGY: LINEAR (ii) MOLECULE TYPE:
         (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 54:

Phe Ala Val Ala Val Ser Ala Val Ser Ser Ala Val Ser Ser Val Ser
 1               5                  10                  15

Ser Ala Val Ser Ser Ala Val Ser Ser Ser Ser
            20                  25

(2) INFORMATION FOR SEQ ID NO: 55:

(i) SEQUENCE CHARACTERISTICS:
            (A) LENGTH: 27
            (B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 55:

Phe Ala Lys Lys Phe Ala Lys Lys Phe Lys Lys Phe Ala Lys Lys Phe
 1               5                  10                  15

Ala Lys Phe Ala Phe Ala Phe Lys Lys Lys Lys
            20                  25

(2) INFORMATION FOR SEQ ID NO: 56:

(i) SEQUENCE CHARACTERISTICS:
            (A) LENGTH: 27
            (B) TYPE: AMINO ACID
            (C) TOPOLOGY: LINEAR (ii) MOLECULE TYPE:
            (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 56:

Lys Lys Lys Lys Phe Ala Lys Lys Phe Ala Lys Lys Phe Lys Lys Phe
 1               5                  10                  15

Ala Lys Lys Phe Ala Lys Phe Ala Phe Ala Phe
            20                  25

(2) INFORMATION FOR SEQ ID NO: 57:

(i) SEQUENCE CHARACTERISTICS:
            (A) LENGTH: 23

(B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 57:

Phe Ala Arg Lys Phe Leu Lys Arg Phe Lys Lys Phe Val Arg Lys Phe
1               5                   10                  15

Ile Arg Phe Ala Phe Leu Phe
            20

(2) INFORMATION FOR SEQ ID NO: 58:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 58:

Phe Ala Arg Lys Phe Leu Lys Arg Phe Lys Lys Phe Val Arg Lys Phe
1               5                   10                  15

Ile Arg Phe Ala Phe Leu Phe Lys Arg Lys Arg
            20                  25

(2) INFORMATION FOR SEQ ID NO: 59:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 59:

Lys Arg Lys Arg Phe Ala Arg Lys Phe Leu Lys Arg Phe Lys Lys Phe
1               5                   10                  15

Val Arg Lys Phe Ile Arg Phe Ala Phe Leu Phe 20                  25

(2) INFORMATION FOR SEQ ID NO: 60:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 60:

Ile Ala Lys Lys Ile Ala Lys Lys Ile Lys Lys Ile Ala Lys Lys Ile
 1               5                  10                  15

Ala Lys Ile Ala Ile Ala Ile
            20

(2) INFORMATION FOR SEQ ID NO: 61:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 61:

Ile Ala Lys Lys Ile Ala Lys Lys Ile Lys Lys Ile Ala Lys Lys Ile
 1               5                  10                  15

Ala Lys Ile Ala Ile Ala Ile Lys Lys Lys Lys
            20                  25

(2) INFORMATION FOR SEQ ID NO: 62:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 62:

Lys Lys Lys Lys Ile Ala Lys Lys Ile Ala Lys Lys Ile Lys Lys Ile
1               5                   10                  15

Ala Lys Lys Ile Ala Lys Ile Ala Ile Ala Ile
            20                  25

(2) INFORMATION FOR SEQ ID NO: 63:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 63:

Ile Ala Arg Lys Ile Leu Lys Arg Ile Lys Lys Ile Val Arg Lys Phe
1               5                   10                  15

Ile Arg Ile Ala Ile Leu Ile
            20

(2) INFORMATION FOR SEQ ID NO: 64:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 64:

Ile Ala Arg Lys Ile Leu Lys Arg Ile Lys Lys Ile Val Arg Lys Phe
1               5                   10                  15

Ile Arg Ile Ala Ile Leu Ile Lys Arg Lys Arg
            20                  25

(2) INFORMATION FOR SEQ ID NO: 65:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 65:

Lys Arg Lys Arg Ile Ala Arg Lys Ile Leu Lys Arg Ile Lys Lys Ile
  1               5                  10                  15

Val Arg Lys Phe Ile Arg Ile Ala Ile Leu Ile
             20                  25

(2) INFORMATION FOR SEQ ID NO: 66:

(i) SEQUENCE CHARACTERISTICS:
             (A) LENGTH: 17
             (B) TYPE: AMINO ACID
             (C) TOPOLOGY: LINEAR (ii) MOLECULE TYPE:
             (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 66:

Phe Lys Leu Arg Ala Lys Ile Lys Val Arg Leu Arg Ala Lys Ile Lys
  1               5                  10                  15

Leu (2) INFORMATION FOR SEQ ID NO: 67:

(i) SEQUENCE CHARACTERISTICS:
             (A) LENGTH: 21
             (B) TYPE: AMINO ACID
             (C) TOPOLOGY: LINEAR (ii) MOLECULE TYPE:
             (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 67:

Lys Arg Lys Arg Phe Lys Leu Arg Ala Lys Ile Lys Val Arg Leu Arg
  1               5                  10                  15

Ala Lys Ile Lys Leu
             20

(2) INFORMATION FOR SEQ ID NO: 68:

(i) SEQUENCE CHARACTERISTICS:
             (A) LENGTH: 21
             (B) TYPE: AMINO ACID
             (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 68:

Phe Lys Leu Arg Ala Lys Ile Lys Val Arg Leu Arg Ala Lys Ile Lys
1               5                  10                  15

Leu Lys Arg Lys Arg
            20

(2) INFORMATION FOR SEQ ID NO: 69:

(i) SEQUENCE CHARACTERISTICS:
         (A) LENGTH: 23
         (B) TYPE: AMINO ACID
         (C) TOPOLOGY: LINEAR (ii) MOLECULE TYPE:
         (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 69:

Phe Lys Leu Arg Ala Lys Ile Lys Val Arg Leu Arg Ala Lys Ile Lys
1               5                  10                  15

Leu Arg Val Lys Leu Lys Ile
            20

(2) INFORMATION FOR SEQ ID NO: 70:

(i) SEQUENCE CHARACTERISTICS:
         (A) LENGTH: 27
         (B) TYPE: AMINO ACID
         (C) TOPOLOGY: LINEAR (ii) MOLECULE TYPE:
         (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 70:

Phe Lys Leu Arg Ala Lys Ile Lys Val Arg Leu Arg Ala Lys Ile Lys
1               5                  10                  15

Leu Arg Val Lys Leu Lys Ile Lys Arg Lys Arg
            20                  25

(2) INFORMATION FOR SEQ ID NO: 71:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 71:

```
Lys Arg Lys Arg Phe Lys Leu Arg Ala Lys Ile Lys Val Arg Leu Arg
 1               5                  10                  15
Ala Lys Ile Lys Leu Arg Val Lys Leu Lys Ile
                20                  25
```

(2) INFORMATION FOR SEQ ID NO: 72:

(i) SEQUENCE CHARACTERISTICS:
        (A) LENGTH: 29
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 72:

```
Phe Lys Leu Arg Ala Lys Ile Lys Val Arg Leu Arg Ala Lys Ile Lys
 1               5                  10                  15
Leu Arg Val Lys Leu Lys Ile Arg Ala Arg Ile Lys Leu
                20                  25
```

(2) INFORMATION FOR SEQ ID NO: 73:

(i) SEQUENCE CHARACTERISTICS:
        (A) LENGTH: 33
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 73:

Phe Lys Leu Arg Ala Lys Ile Lys Val Arg Leu Arg Ala Lys Ile Lys
1               5                   10                  15

Leu Arg Val Lys Leu Lys Ile Arg Ala Arg Ile Lys Leu Lys Arg Lys
                20                  25                  30

Arg (2) INFORMATION FOR SEQ ID NO: 74:

(i) SEQUENCE CHARACTERISTICS:
        (A) LENGTH: 33
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 74:

Lys Arg Lys Arg Phe Lys Leu Arg Ala Lys Ile Lys Val Arg Leu Arg
1               5                   10                  15

Ala Lys Ile Lys Leu Arg Val Lys Leu Lys Ile Arg Ala Arg Ile Lys
                20                  25                  30

Leu (2) INFORMATION FOR SEQ ID NO: 75:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 75:

Phe Lys Leu Arg Ala Lys Ile Lys Val Arg Leu Arg Ala Lys Ile Lys
1               5                   10                  15

Leu Val Phe Ala Ile Leu Leu
                20

(2) INFORMATION FOR SEQ ID NO: 76:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 76:

Phe Lys Leu Arg Ala Lys Ile Lys Val Arg Leu Arg Ala Lys Ile Lys
1               5                  10                  15

Leu Val Phe Ala Ile Leu Leu Lys Arg Lys Arg
                20                  25

(2) INFORMATION FOR SEQ ID NO: 77:

(i) SEQUENCE CHARACTERISTICS:
          (A) LENGTH: 27
          (B) TYPE: AMINO ACID
          (C) TOPOLOGY: LINEAR (ii) MOLECULE TYPE:
          (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 77:

Lys Arg Lys Arg Phe Lys Leu Arg Ala Lys Ile Lys Val Arg Leu Arg
1               5                  10                  15

Ala Lys Ile Lys Leu Val Phe Ala Ile Leu Leu
                20                  25

(2) INFORMATION FOR SEQ ID NO: 78:

(i) SEQUENCE CHARACTERISTICS:
          (A) LENGTH: 23
          (B) TYPE: AMINO ACID
          (C) TOPOLOGY: LINEAR (ii) MOLECULE TYPE:
          (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 78:

Val Phe Ala Ile Leu Leu Phe Lys Leu Arg Ala Lys Ile Lys Val Arg
1               5                  10                  15

Leu Arg Ala Lys Ile Lys Leu
                20

(2) INFORMATION FOR SEQ ID NO: 79:

(i) SEQUENCE CHARACTERISTICS:

(A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 79:

Val Phe Ala Ile Leu Leu Phe Lys Leu Arg Ala Lys Ile Lys Val Arg
 1               5                  10                  15
Leu Arg Ala Lys Ile Lys Leu Lys Arg Lys Arg
                20                  25

(2) INFORMATION FOR SEQ ID NO: 80:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 80:

Lys Arg Lys Arg Val Phe Ala Ile Leu Leu Phe Lys Leu Arg Ala Lys
 1               5                  10                  15
Ile Lys Val Arg Leu Arg Ala Lys Ile Lys Leu
                20                  25

(2) INFORMATION FOR SEQ ID NO: 81:

(i) SEQUENCE CHARACTERISTICS:
        (A) LENGTH: 29
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 81:

Val Gly Glu Cys Val Arg Gly Arg Cys Pro Ser Gly Met Cys Cys Ser
 1               5                  10                  15

```
Gln Phe Gly Tyr Cys Gly Lys Gly Pro Lys Tyr Cys Gly
            20                  25
```

(2) INFORMATION FOR SEQ ID NO: 82:

(i) SEQUENCE CHARACTERISTICS:
        (A) LENGTH: 30
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 82:

```
Val Gly Glu Cys Val Arg Gly Arg Cys Pro Ser Gly Met Cys Cys Ser
1               5                   10                  15
Gln Phe Gly Tyr Cys Gly Lys Gly Pro Lys Tyr Cys Gly Arg
            20                  25                  30
```

(2) INFORMATION FOR SEQ ID NO: 83:

(i) SEQUENCE CHARACTERISTICS:
        (A) LENGTH: 30
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 83:

```
Leu Gly Asp Cys Leu Lys Gly Lys Cys Pro Ser Gly Met Cys Cys Ser
1               5                   10                  15
Asn Tyr Gly Phe Cys Gly Arg Gly Pro Arg Phe Cys Gly Lys
            20                  25                  30
```

(2) INFORMATION FOR SEQ ID NO: 84:

(i) SEQUENCE CHARACTERISTICS:
        (A) LENGTH: 37
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 84:

Gln Cys Ile Gly Asn Gly Gly Arg Cys Asn Glu Asn Val Gly Pro Pro
1               5                   10                  15

Tyr Cys Cys Ser Gly Phe Cys Leu Arg Gln Pro Gly Gln Gly Tyr Gly
                20                  25                  30

Tyr Cys Lys Asn Arg
        35

(2) INFORMATION FOR SEQ ID NO: 85:

(i) SEQUENCE CHARACTERISTICS:
        (A) LENGTH: 36
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 85:

Cys Ile Gly Asn Gly Gly Arg Cys Asn Glu Asn Val Gly Pro Pro Tyr
1               5                   10                  15

Cys Cys Ser Gly Phe Cys Leu Arg Gln Pro Asn Gln Gly Tyr Gly Val
                20                  25                  30

Cys Arg Asn Arg
        35

(2) INFORMATION FOR SEQ ID NO: 86:

(i) SEQUENCE CHARACTERISTICS:
        (A) LENGTH: 36
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 86:

Cys Ile Gly Gln Gly Gly Lys Cys Gln Asp Gln Leu Gly Pro Pro Phe
1               5                   10                  15

Cys Cys Ser Gly Tyr Cys Val Lys Asn Pro Gln Asn Gly Phe Gly Leu
                20                  25                  30

Cys Lys Gln Lys
        35

(2) INFORMATION FOR SEQ ID NO: 87:

(i) SEQUENCE CHARACTERISTICS:
                (A) LENGTH: 44
                (B) TYPE: AMINO ACID
                (C) TOPOLOGY: LINEAR (ii) MOLECULE TYPE:
                (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 87:

Gln Lys Leu Cys Glu Arg Pro Ser Gly Thr Trp Ser Gly Val Cys Gly
  1               5                  10                  15

Asn Asn Asn Ala Cys Lys Asn Gln Cys Ile Asn Leu Glu Lys Ala Arg
                 20                  25                  30

His Gly Ser Cys Asn Tyr Val Phe Pro Ala His Lys
             35                  40

(2) INFORMATION FOR SEQ ID NO: 88:

(i) SEQUENCE CHARACTERISTICS:
                (A) LENGTH: 44
                (B) TYPE: AMINO ACID
                (C) TOPOLOGY: LINEAR (ii) MOLECULE TYPE:
                (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 88:

Gln Arg Val Cys Asp Lys Pro Ser Gly Thr Trp Ser Gly Leu Cys Gly
  1               5                  10                  15

Asn Asn Asn Ala Cys Arg Gln Asn Cys Ile Gln Val Asp Arg Ala Lys
                 20                  25                  30

Lys Gly Ser Cys Gln Phe Leu Tyr Pro Ala Lys Lys
             35                  40

(2) INFORMATION FOR SEQ ID NO: 89:

(i) SEQUENCE CHARACTERISTICS:
                (A) LENGTH: 36
                (B) TYPE: AMINO ACID
                (C) TOPOLOGY: LINEAR (ii) MOLECULE TYPE:
                (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 89:

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
                20                  25                  30

His Gly Ser Cys
        35

(2) INFORMATION FOR SEQ ID NO: 90:

(i) SEQUENCE CHARACTERISTICS:
        (A) LENGTH: 36
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 90:

Gln Arg Val Cys Asn Lys Pro Ser Gly Thr Trp Ser Gly Leu Cys Gly
1               5                   10                  15

Asn Asn Asn Ala Cys Arg Gln Asn Cys Ile Lys Val Asp Arg Ala Lys
                20                  25                  30

Lys Gly Ser Cys
        35

(2) INFORMATION FOR SEQ ID NO: 91:

(i) SEQUENCE CHARACTERISTICS:
        (A) LENGTH: 20
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 91:

Met Leu Glu Glu Leu Phe Glu Glu Met Thr Glu Phe Ile Glu Glu Val
1               5                   10                  15

Ile Glu Thr Met
        20

(2) INFORMATION FOR SEQ ID NO: 92:

(i) SEQUENCE CHARACTERISTICS:
        (A) LENGTH: 1228
        (B) TYPE: NUCLEIC ACID (C) STRANDEDNESS: DOUBLE STRANDED
(D) TOPOLOGY: LINEAR (ii) MOLECULE TYPE:
(A) DESCRIPTION: GENOMIC DNA AND OTHER NUCLEIC ACID (xi) SEQUENCE DESCRIPTION: SEQ ID NO: 92:

```
CCAAAGCACA TACTTATCGA TTTAAATTTC ATCGAAGAGA TTAATATCGA              50

ATAATCATAT ACATACTTTA AATACATAAC AAATTTTAAA TACATATATC             100

TGGTATATAA TTAATTTTTT AAAGTCATGA AGTATGTATC AAATACACAT             150

ATGGAAAAAA TTAACTATTC ATAATTTAAA AAATAGAAAA GATACATCTA             200

GTGAAATTAG GTGCATGTAT CAAATACATT AGGAAAAGGG CATATATCTT             250

GATCTAGATA ATTAACGATT TGATTTATG TATAATTTCC AAATGAAGGT              300

TTATATCTAC TTCAGAAATA ACAATATACT TTTATCAGAA CATTCAACAA             350

AGCAACAACC AACTAGAGTG AAAAATACAC ATTGTTCTCT AGACATACAA             400

AATTGAGAAA AGAATCTCAA AATTTAGAGA AACAAATCTG AATTTCTAGA             450

AGAAAAAAAT AATTATGCAC TTTGCTATTG CTCGAAAAAT AAATGAAAGA             500

AATTAGACTT TTTTAAAAGA TGTTAGACTA GATATACTCA AAAGCTATTA             550

AAGGAGTAAT ATTCTTCTTA CATTAAGTAT TTTAGTTACA GTCCTGTAAT             600

TAAAGACACA TTTTAGATTG TATCTAAACT TAAATGTATC TAGAATACAT             650

ATATTTGAAT GCATCATATA CATGTATCCG ACACACCAAT TCTCATAAAA             700

AACGTAATAT CCTAAACTAA TTTATCCTTC AAGTCAACTT AAGCCCAATA             750

TACATTTTCA TCTCTAAAGG CCCAAGTGGC ACAAAATGTC AGGCCCAATT             800

ACGAAGAAAA GGGCTTGTAA AACCCTAATA AAGTGGCACT GGCAGAGCTT             850

ACACTCTCAT TCCATCAACA AAGAAACCCT AAAAGCCGCA GCGCCACTGA             900

TTTCTCTCCT CCAGGCGAAG ATG CAG ATC TTC GTG AAG ACC TTA              944
                      Met Gln Ile Phe Val Lys Thr Leu
                       1               5

ACG GGG AAG ACG ATC ACC CTA GAG GTT GAG TCT TCC GAC ACC            986
Thr Gly Lys Thr Ile Thr Leu Glu Val Glu Ser Ser Asp Thr
 10              15                  20

ATC GAC AAT GTC AAA GCC AAG ATC CAG GAC AAG GAA GGG ATT           1028
Ile Asp Asn Val Lys Ala Lys Ile Gln Asp Lys Glu Gly Ile
     25                  30                  35

CCC CCA GAC CAG CAG CGT TTG ATT TTC GCC GGA AAG CAG CTT           1070
Pro Pro Asp Gln Gln Arg Leu Ile Phe Ala Gly Lys Gln Leu
             40                  45                  50

GAG GAT GGT CGT ACT CTT GCC GAC TAC AAC ATC CAG AAG GAG           1112
Glu Asp Gly Arg Thr Leu Ala Asp Tyr Asn Ile Gln Lys Glu
                 55                  60

TCA ACT CTC CAT CTC GTG CTC CGT CTC CGT GGT GGT                   1148
Ser Thr Leu His Leu Val Leu Arg Leu Arg Gly Gly
 65              70                  75

GGA TCC GCT GTT AAA AGA GTG GGT CGT AGG TTG AAA AAG TTG           1190
Gly Ser Ala Val Lys Arg Val Gly Arg Arg Leu Lys Lys Leu
             80                  85                  90

GAC CGT AAG ATT GAT AGG TTA GGA GTT GAT TTT TGATC                 1228
Asp Arg Lys Ile Asp Arg Leu Gly Val Asp Phe
                 95                  100
```

(2) INFORMATION FOR SEQ ID NO: 93:

(i) SEQUENCE CHARACTERISTICS:

(A) LENGTH: 1154
        (B) TYPE: NUCLEIC ACID
        (C) STRANDEDNESS: DOUBLE STRANDED
        (D) TOPOLOGY: LINEAR (ii) MOLECULE TYPE:
        (A) DESCRIPTION: GENOMIC DNA (xi) SEQUENCE DESCRIPTION: SEQ ID NO: 93:

```
CCAAAGCACA TACTTATCGA TTTAAATTTC ATCGAAGAGA TTAATATCGA            50

ATAATCATAT ACATACTTTA AATACATAAC AAATTTTAAA TACATATATC            100

TGGTATATAA TTAATTTTTT AAAGTCATGA AGTATGTATC AAATACACAT            150

ATGGAAAAAA TTAACTATTC ATAATTTAAA AAATAGAAAA GATACATCTA            200

GTGAAATTAG GTGCATGTAT CAAATACATT AGGAAAAGGG CATATATCTT            250

GATCTAGATA ATTAACGATT TTGATTTATG TATAATTTCC AAATGAAGGT            300

TTATATCTAC TTCAGAAATA ACAATATACT TTTATCAGAA CATTCAACAA            350

AGCAACAACC AACTAGAGTG AAAAATACAC ATTGTTCTCT AGACATACAA            400

AATTGAGAAA AGAATCTCAA AATTTAGAGA AACAAATCTG AATTTCTAGA            450

AGAAAAAAAT AATTATGCAC TTTGCTATTG CTCGAAAAAT AAATGAAAGA            500

AATTAGACTT TTTTAAAAGA TGTTAGACTA GATATACTCA AAAGCTATTA            550

AAGGAGTAAT ATTCTTCTTA CATTAAGTAT TTTAGTTACA GTCCTGTAAT            600

TAAAGACACA TTTTAGATTG TATCTAAACT TAAATGTATC TAGAATACAT            650

ATATTTGAAT GCATCATATA CATGTATCCG ACACACCAAT TCTCATAAAA            700

AACGTAATAT CCTAAACTAA TTTATCCTTC AAGTCAACTT AAGCCCAATA            750

TACATTTTCA TCTCTAAAGG CCCAAGTGGC ACAAAATGTC AGGCCCAATT            800

ACGAAGAAAA GGGCTTGTAA AACCCTAATA AAGTGGCACT GGCAGAGCTT            850

ACACTCTCAT TCCATCAACA AAGAAACCCT AAAAGCCGCA GCGCCACTGA            900

TTTCTCTCCT CCAGGCGAAG ATG CAG ATC TTC GTG AAG ACC TTA            944
                      Met Gln Ile Phe Val Lys Thr Leu
                       1               5

ACG GGG AAG ACG ATC ACC CTA GAG GTT GAG TCT TCC GAC ACC           986
Thr Gly Lys Thr Ile Thr Leu Glu Val Glu Ser Ser Asp Thr
 10              15                  20

ATC GAC AAT GTC AAA GCC AAG ATC CAG GAC AAG GAA GGG ATT          1028
Ile Asp Asn Val Lys Ala Lys Ile Gln Asp Lys Glu Gly Ile
         25                  30                  35

CCC CCA GAC CAG CAG CGT TTG ATT TTC GCC GGA AAG CAG CTT          1070
Pro Pro Asp Gln Gln Arg Leu Ile Phe Ala Gly Lys Gln Leu
             40                  45                  50

GAG GAT GGT CGT ACT CTT GCC GAC TAC AAC ATC CAG AAG GAG          1112
Glu Asp Gly Arg Thr Leu Ala Asp Tyr Asn Ile Gln Lys Glu
                 55                  60

TCA ACT CTC CAT CTC GTG CTC CGT CTC CGT GGT GGT GGA TCC          1154
Ser Thr Leu His Leu Val Leu Arg Leu Arg Gly Gly Gly Ser
 65              70                  75
```

(2) INFORMATION FOR SEQ ID NO: 94:

(i) SEQUENCE CHARACTERISTICS:
        (A) LENGTH: 78
        (B) TYPE: AMINO ACID
        (D) TOPOLOGY: LINEAR (ii) MOLECULE TYPE:
        (A) DESCRIPTION: PEPTIDE (xi) SEQUENCE DESCRIPTION: SEQ ID NO: 94:

```
Met Gln Ile Phe Val Lys Thr Leu
 1               5

Thr Gly Lys Thr Ile Thr Leu Glu Val Glu Ser Ser Asp Thr
     10              15                  20

Ile Asp Asn Val Lys Ala Lys Ile Gln Asp Lys Glu Gly Ile
         25                  30                  35

Pro Pro Asp Gln Gln Arg Leu Ile Phe Ala Gly Lys Gln Leu
             40                  45                  50

Glu Asp Gly Arg Thr Leu Ala Asp Tyr Asn Ile Gln Lys Glu
                 55                  60

Ser Thr Leu His Leu Val Leu Arg Leu Arg Gly Gly Gly Ser
 65              70                  75
```

(2) INFORMATION FOR SEQ ID NO: 95:

(i) SEQUENCE CHARACTERISTICS:
        (A) LENGTH: 2127
        (B) TYPE: NUCLEIC ACID
        (C) STRANDEDNESS: DOUBLE STRANDED
        (D) TOPOLOGY: LINEAR (ii) MOLECULE TYPE:
        (A) DESCRIPTION: GENOMIC DNA AND OTHER DNA (xi) SEQUENCE DESCRIPTION: SEQ ID NO: 95:

| | |
|---|---:|
| TTTATCAATC AGATTTGAAC ATATAAATAA ATATAAATTG TCTCAATAAT | 50 |
| TCTACATTAA ACTAATATTT GAAATCTCAA TTTTATGATT TTTTAAATTC | 100 |
| ACTTTATATC CAAGACAATT TNCANCTTCA AAAAGTTTTA TTAAANATTT | 150 |
| ACATTAGTTT TGTTGATGAG GATGACAAGA TNTTGGTCAT CAATTACATA | 200 |
| TACCCAAATT GAATAGTAAG CAACTTCAAT GTTTTTCATA ATGATAATGA | 250 |
| CAGACACAAN NNAAACCCAT TTATTATTCA CATTGATTGA GTTTTATATG | 300 |
| CAATATAGTA ATAATAATAA TATTTCTTAT AAAGCAAGAG GTCAATTTTT | 350 |
| TTTTAATTAT ACCACGTCAC TAAATTATAT TTGATAATGT AAAACAATTC | 400 |
| AAATTTTACT TAAATATCAT GAAATAAACT ATTTTTATAA CCAAATTACT | 450 |
| AAATTTTTCC AATAAAAAAA AGTCATTAAG AAGACATAAA ATAAATTTGA | 500 |
| GGTAAANGAG TGAAGTCGAC TGACTTTTTT TTTTTTTATC ATAAGAAAAT | 550 |
| AAATTATTAA CTTTAACCTA ATAAAACACT AATATAATTT CATGGAATCT | 600 |
| AATACTTACC TCTTAGAAAT AAGAAAAAGT GTTTCTAATA GACCCTCAAT | 650 |
| TTACATTAAA TATTTTCAAT CAAATTTAAA TAACAAATAT CAATATGAGG | 700 |
| TCAATAACAA TATCAAAATA ATATGAAAAA AGAGCAATAC ATAATATAAG | 750 |
| GGACGATTTA AGTGCGATTA TCAAGGTAGT ATTATATCCT AATTTGCTAA | 800 |
| TATTTGNGCT CTTATATTTA AGGTCATGTT CATGATAAAC TTGAAATGCG | 850 |
| CTATATTAGA GCATATATTA AAATAAAAAA ATACCTAAAA TAAAATTAAG | 900 |
| TTATTTTTAG TATATATTTT TTTACATGAC CTACATTTTT CTGGGTTTTT | 950 |
| CTAAAGGAGC GTGTAAGTGT CGACCTCATT CTCCTAATTT TCCCCACCAC | 1000 |
| ATAAAAATTA AAAAGGAAAG GTAGCTTTTG CGTGTTGTTT TGGTACACTA | 1050 |
| CACCTCATTA TTACACGTGT CCTCATATAA TTGGTTAACC CTATGAGGCG | 1100 |
| GTTTCGTCTA GAGTCGGCCA TGCCATCTAT AAAATGAAGC TTTCTGCACC | 1150 |

```
TCATTTTTTT CATCTTCTAT CTGATTTCTA TTATAATTTC TCTCAATTGC            1200

CTTCAAATTT CTCTTTAAGG TTAGAATCTT CTCTATTTTT                       1240

GGTTTTTGTA TGTTTAGATT CTCGAATTAG CTAATCAGGC GCTGTTATAG            1290

CCCTTCCTTT TGAGTCTCTC CTCGGTTGTC TTGATGGAAA AGGCCTAACA            1340

TTTGAGTTTT TTTACGTCTG GTTTGATGGA AAAGGCCTAC AATTGGCCGT            1390

TTTCCCCGTT CGTTTTGATG AAAAAGCCCC TAGTTTGAGA TTTTTTTTCT            1440

GTCGTTCGTT CTAAAGGTTT AAAATTAGAG TTTTTACATT TGTTTGATGA            1490

AAAAGGCCTT AAATTTGAGT TTTTCCGGTT GATTTGATGA AAAAGCCCTA            1540

GAATTTGTGT TTTTCCGTCG GTTTGATTCT GAAGGCCTAA AATTTGAGTT            1590

TCTCCGGCTG TTTTGATGAA AAAGCCCTAA ATTTGAGTTT CTCCGGCTGT            1640

TTTGATGAAA AAGCCCTAAA TTTGAAGTTT TTCCCCGTG TTTTAGATTG             1690

TTTAGGTTTT AATTCTCGAA TCAGCTAATC AGGGAGTGTG AAAGCCCTAA            1740

ATTGAAGTTT TTTCGTTGT TCTGATTGTT GTTTTTATGA ATTTGCAG               1788

ATG CAG ATC TTT GTG AAA ACT CTC ACC GGA AAG ACT ATC ACC           1830
Met Gln Ile Phe Val Lys Thr Leu Thr Gly Lys Thr Ile Thr
 1               5                  10

CTA GAG GTG GAA AGT TCT GAT ACA ATC GAC AAC GTT AAG GCT           1872
Leu Glu Val Glu Ser Ser Asp Thr Ile Asp Asn Val Lys Ala
15                  20                  25

AAG ATC CAG GAT AAG GAA GGA ATT CCC CCG GAT CAG CAA AGG           1914
Lys Ile Gln Asp Lys Glu Gly Ile Pro Pro Asp Gln Gln Arg
        30                  35                  40

CTT ATC TTC GCC GGA AAG CAG TTG GAG GAC GGA CGT ACT CTA           1956
Leu Ile Phe Ala Gly Lys Gln Leu Glu Asp Gly Arg Thr Leu
            45                  50                  55

GCT GAT TAC AAC ATC CAG AAG GAG TCT ACC CTC CAT TTG GTG           1998
Ala Asp Tyr Asn Ile Gln Lys Glu Ser Thr Leu His Leu Val
                60                  65                  70

CTC CGT CTA CGT GGA GGT GGA TCC GCT GTT AAA AGA GTG GGT           2040
Leu Arg Leu Arg Gly Gly Gly Ser Ala Val Lys Arg Val Gly
                    75                  80

CGT AGG TTG AAA AAG TTG GAC CGT AAG ATT GAT AGG TTA GGA           2082
Arg Arg Leu Lys Lys Leu Asp Arg Lys Ile Asp Arg Leu Gly
85                  90                  95

GTT GAT TTT TGATCTAGAG TCGACCGATC CCCCGAATTT CCCCGA               2127
Val Asp Phe
    100

(2) INFORMATION FOR SEQ ID NO: 96:

(i) SEQUENCE CHARACTERISTICS:
        (A) LENGTH: 2022
        (B) TYPE: NUCLEIC ACID
        (C) STRANDEDNESS: DOUBLE STRANDED
        (D) TOPOLOGY: LINEAR (ii) MOLECULE TYPE:
        (A) DESCRIPTION: GENOMIC DNA (xi) SEQUENCE DESCRIPTION: SEQ ID NO: 96:

TTTATCAATC AGATTTGAAC ATATAAATAA ATATAAATTG TCTCAATAAT              50

TCTACATTAA ACTAATATTT GAAATCTCAA TTTTATGATT TTTTAAATTC             100

ACTTTATATC CAAGACAATT TNCANCTTCA AAAAGTTTTA TTAAANATTT             150

ACATTAGTTT TGTTGATGAG GATGACAAGA TNTTGGTCAT CAATTACATA             200
```

```
TACCCAAATT GAATAGTAAG CAACTTCAAT GTTTTTCATA ATGATAATGA         250

CAGACACAAN NNAAACCCAT TTATTATTCA CATTGATTGA GTTTTATATG         300

CAATATAGTA ATAATAATAA TATTTCTTAT AAAGCAAGAG GTCAATTTTT         350

TTTTAATTAT ACCACGTCAC TAAATTATAT TTGATAATGT AAAACAATTC         400

AAATTTTACT TAAATATCAT GAAATAAACT ATTTTTATAA CCAAATTACT         450

AAATTTTTCC AATAAAAAAA AGTCATTAAG AAGACATAAA ATAAATTTGA         500

GGTAAANGAG TGAAGTCGAC TGACTTTTTT TTTTTTTATC ATAAGAAAAT         550

AAATTATTAA CTTTAACCTA ATAAAACACT AATATAATTT CATGGAATCT         600

AATACTTACC TCTTAGAAAT AAGAAAAAGT GTTTCTAATA GACCCTCAAT         650

TTACATTAAA TATTTTCAAT CAAATTTAAA TAACAAATAT CAATATGAGG         700

TCAATAACAA TATCAAAATA ATATGAAAAA AGAGCAATAC ATAATATAAG         750

GGACGATTTA AGTGCGATTA TCAAGGTAGT ATTATATCCT AATTTGCTAA         800

TATTTGNGCT CTTATATTTA AGGTCATGTT CATGATAAAC TTGAAATGCG         850

CTATATTAGA GCATATATTA AAATAAAAAA ATACCTAAAA TAAAATTAAG         900

TTATTTTTAG TATATATTTT TTTACATGAC CTACATTTTT CTGGGTTTTT         950

CTAAAGGAGC GTGTAAGTGT CGACCTCATT CTCCTAATTT TCCCCACCAC        1000

ATAAAAATTA AAAAGGAAAG GTAGCTTTTG CGTGTTGTTT TGGTACACTA        1050

CACCTCATTA TTACACGTGT CCTCATATAA TTGGTTAACC CTATGAGGCG        1100

GTTTCGTCTA GAGTCGGCCA TGCCATCTAT AAAATGAAGC TTTCTGCACC        1150

TCATTTTTTT CATCTTCTAT CTGATTTCTA TTATAATTTC TCTCAATTGC        1200

CTTCAAATTT CTCTTTAAGG TTAGAATCTT CTCTATTTTT                   1240

GGTTTTTGTA TGTTTAGATT CTCGAATTAG CTAATCAGGC GCTGTTATAG        1290

CCCTTCCTTT TGAGTCTCTC CTCGGTTGTC TTGATGGAAA AGGCCTAACA        1340

TTTGAGTTTT TTTACGTCTG GTTTGATGGA AAAGGCCTAC AATTGGCCGT        1390

TTTCCCCGTT CGTTTTGATG AAAAAGCCCC TAGTTTGAGA TTTTTTTTCT        1440

GTCGTTCGTT CTAAAGGTTT AAAATTAGAG TTTTTACATT TGTTTGATGA        1490

AAAAGGCCTT AAATTTGAGT TTTTCCGGTT GATTGATGA AAAAGCCCTA         1540

GAATTTGTGT TTTTCCGTCG GTTGATTCT GAAGGCCTAA AATTTGAGTT         1590

TCTCCGGCTG TTTTGATGAA AAAGCCCTAA ATTTGAGTTT CTCCGGCTGT        1640

TTTGATGAAA AGCCCTAAA TTTGAAGTTT TTTCCCCGTG TTTTAGATTG         1690

TTTAGGTTTT AATTCTCGAA TCAGCTAATC AGGGAGTGTG AAAGCCCTAA        1740

ATTGAAGTTT TTTTCGTTGT TCTGATTGTT GTTTTTATGA ATTTGCAG         1788

ATG CAG ATC TTT GTG AAA ACT CTC ACC GGA AAG ACT ATC ACC       1830
Met Gln Ile Phe Val Lys Thr Leu Thr Gly Lys Thr Ile Thr
 1               5                    10

CTA GAG GTG GAA AGT TCT GAT ACA ATC GAC AAC GTT AAG GCT       1872
Leu Glu Val Glu Ser Ser Asp Thr Ile Asp Asn Val Lys Ala
15                  20                  25

AAG ATC CAG GAT AAG GAA GGA ATT CCC CCG GAT CAG CAA AGG       1914
Lys Ile Gln Asp Lys Glu Gly Ile Pro Pro Asp Gln Gln Arg
     30                  35                  40

CTT ATC TTC GCC GGA AAG CAG TTG GAG GAC GGA CGT ACT CTA       1956
Leu Ile Phe Ala Gly Lys Gln Leu Glu Asp Gly Arg Thr Leu
         45                  50                  55
```

```
GCT GAT TAC AAC ATC CAG AAG GAG TCT ACC CTC CAT TTG GTG              1998
Ala Asp Tyr Asn Ile Gln Lys Glu Ser Thr Leu His Leu Val
            60                  65                  70

CTC CGT CTA CGT GGA GGT GGA TCC                                      2022
Leu Arg Leu Arg Gly Gly Gly Ser
                75
```

(2) INFORMATION FOR SEQ ID NO: 97:

(i) SEQUENCE CHARACTERISTICS:
        (A) LENGTH: 37
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 97:

```
Lys Arg Lys Arg Ala Val Lys Val Gly Arg Arg Leu Lys Lys Leu
 1               5                  10                  15

Ala Arg Lys Ile Ala Arg Leu Gly Val Ala Lys Leu Ala Gly Leu Arg
            20                  25                  30

Ala Val Leu Lys Phe
        35
```

(2) INFORMATION FOR SEQ ID NO: 98:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 98:

```
Ala Val Lys Arg Val Gly Arg Arg Leu Lys Lys Leu Asp Arg Lys Ile
 1               5                  10                  15

Asp Arg Leu Gly Val Asp Phe
            20
```